United States Patent
Kizhakkedathu et al.

(10) Patent No.: US 10,202,507 B2
(45) Date of Patent: Feb. 12, 2019

(54) ANTITHROMBOTIC COMPOUNDS, METHODS AND USES THEREOF

(71) Applicants: The University of British Columbia, Vancouver (CA); The Board of Trustees of the University of Illinois, Urbana, IL (US)

(72) Inventors: Jayachandran Kizhakkedathu, New Westminster (CA); James H. Morrissey, Champaign, IL (US); Richard J. Travers, Champaign, IL (US); Rajesh Shenoi, Richmond (CA); Manu Thomas Kalathottukaren, Vancouver (CA)

(73) Assignees: The University of British Columbia, Vancouver (CA); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/313,774

(22) PCT Filed: May 29, 2015

(86) PCT No.: PCT/CA2015/000353
§ 371 (c)(1),
(2) Date: Nov. 23, 2016

(87) PCT Pub. No.: WO2015/179958
PCT Pub. Date: Dec. 3, 2015

(65) Prior Publication Data
US 2017/0233573 A1    Aug. 17, 2017

Related U.S. Application Data

(60) Provisional application No. 62/004,866, filed on May 29, 2014.

(51) Int. Cl.
| | | |
|---|---|---|
| C08L 79/02 | (2006.01) | |
| A61K 31/785 | (2006.01) | |
| C08L 101/00 | (2006.01) | |
| A61K 9/00 | (2006.01) | |

(52) U.S. Cl.
CPC ............ *C08L 79/02* (2013.01); *A61K 9/0019* (2013.01); *A61K 31/785* (2013.01); *C08L 101/005* (2013.01); *C08L 2203/02* (2013.01); *C08L 2207/53* (2013.01)

(58) Field of Classification Search
CPC ...... C08L 2207/53; A61K 31/785; A61K 9/19
USPC ........................................................ 424/400
See application file for complete search history.

(56) References Cited

U.S. PATENT DOCUMENTS

2009/0012033 A1*  1/2009  DeMattei ............. A61K 9/5146
                                                514/44 R

FOREIGN PATENT DOCUMENTS

| CA | 2622021 | 3/2007 |
|----|---------|--------|
| CA | 2658338 | 1/2008 |
| CA | 2871277 | 10/2013 |
| WO | 2006115547 | 11/2006 |
| WO | 2010000713 | 1/2010 |
| WO | 2012162789 | 12/2012 |

OTHER PUBLICATIONS

K Poon, et al.; title: Polymeric hydrophilic polymers in targeted drug delivery artificial Cells, Cell Engineering and Therapy, A volume in Woodhead Publishing Series in Biomaterials, pp. 42-71, 2007.*
Jones, Clinton F., et al., (2012) "Cationic PAMAM dendrimers aggressively initiate blood clot formation", ACS nano., 6(11):1-20.
Ainle, Fionnuala Ni, et al., (2009) "Protamine sulphate down-regultes thrombin generation by inhibiting factor V activation", Blood, 114(8):1658-1665.
Shenoi, Rajesh A., et al., (2014) "Affinity-based design and discovery of a synthetic universal reversal agent for clinically used parenteral heparin anticoagulants", Sci Transl Med, 6(260):1-16.
Jain, Shashank, et al., (2012) "Nucleic acid scavengers inhibit thrombosis without increasing bleeding", Proc Natl Acad Sci U S A, 109(32):12938-43.
Fuchs, Tobias, et al., (2010) "Extracellular DNA traps promote thrombosis", Proceedings of the National Academy of Sciences of the United States of America, 107(36):15880-5.
Travers et al., Blood, Nov. 20, 2014, vol. 124, No. 22, p. 3183-3190.
Shenoi et al., Science Translational Medicine, 2014, 6(260), 1-14.
Mohammadifar et al., ACS Macro Letters, 2017, 6, 35-40.
Sunder et al., Macromolecules, 1999, 32, 4240-4246.
Imran Ul-Haq et al., Macromolecular Bioscience, 2014, 14, 1469-1482.

* cited by examiner

*Primary Examiner* — Yanzhi Zhang
(74) *Attorney, Agent, or Firm* — Rudy J. Ng; Carol L. Francis; Boziecevic, Field & Francis LLP

(57) ABSTRACT

Provided herein are polymers and methods for their use in binding a phosphate containing biological macromolecules. Specifically, the methods and uses provided herein may be used to inhibit thrombin binding to polyphosphate or as an antithrombotic agent for the treatment of stroke, acute coronary syndrome, pulmonary embolism, atrial fibrillation, venous and arterial thromboembolism, disseminated intravascular coagulation (DIC), deep-vein thrombosis (DVT), peripheral artery disease, trauma-induced coagulopathy, extracorporeal circulation, cancer-associated thrombosis, sepsis, septic shock, Systemic Inflammatory Response Syndrome (SIRS), or inflammation.

17 Claims, 25 Drawing Sheets

C

A

B

A

B

C

D

E

ANTITHROMBOTIC COMPOUNDS, METHODS AND USES THEREOF

CROSS REFERENCE TO RELATED APPLICATIONS

This application claims the benefit of U.S. Provisional Patent Application Ser. No. 62/004,866 filed on 29 May 2014 entitled "ANTITHROMBOTIC COMPOUNDS".

STATEMENT REGARDING FEDERALLY SPONSORED RESEARCH

This invention was made with government support under contract numbers R01 HL047014, awarded by the National Institutes of Health, and AHA Predoctoral Fellowship 13PRE14550007, awarded by the American Heart Association. The government has certain rights in the invention.

TECHNICAL FIELD

This invention relates to therapeutics, their uses and methods for the inhibition of thrombosis. In particular the invention relates to therapies and methods of treatment for stroke, heart attack, or pulmonary embolism.

BACKGROUND

Polyphosphate (polyP) is a highly anionic, linear polymer of inorganic phosphate that accumulates in many infectious microorganisms (1) and is secreted by activated human platelets (2). The platelet polyP acts as a procoagulant stimulus at a number of points in the coagulation cascade including: accelerating factor V activation, antagonizing the anticoagulant function of tissue factor pathway inhibitor (TFPI), making clots more resistant to fibrinolysis, and enhancing factor XI activation by thrombin (3). Although, current understanding of the mechanisms behind polyP's acceleration of clotting and which mechanisms are most relevant in vivo, are incomplete. The role of platelet polyP in hemostasis and thrombosis suggests that it may contribute more heavily to thrombosis. Additionally, its role as an accelerant rather than a key enzyme in the final common pathway of the coagulation cascade (unlike, for example, thrombin or factor Xa), suggests that platelet polyP is an attractive therapeutic target for novel antithrombotics with potentially decreased bleeding risk compared to conventional therapies (4). Current antithrombotic drugs used in a clinical setting include, heparin, which has significant toxicity in cell culture (5) and carries risk of major bleeding events and heparin-induced thrombocytopenia, even in heparin-naïve patients (6, 7).

Cationic polymers make attractive candidates for high-affinity polyP inhibitors, and such polymers, including polyethylenimine (PEI) and polyamidoamine (PAMAM) dendrimers, have proven effective in attenuating thrombosis in proof-of-principle studies that identified polyP as a therapeutic target (8, 9). Both of these types of polymers are positively charged due the presence of multiple primary amines, which allows them to bind to and inhibit polyP, but this property can also promote binding to proteins and cell surfaces and thus lead to cellular toxicity, platelet activation, and coagulopathy mediated by fibrinogen aggregation (10, 11). This severely limits the real-world usefulness of these previously identified polyP inhibitors.

SUMMARY

The present invention is based, in part, on the surprising discovery that some polymers that are Universal Heparin Reversal Agents (UHRAs) having low molecular weight and higher charge density as described herein are useful as polyphosphate (polyP) inhibitors and thus may be useful as antithrombotic agents (i.e. as inhibitors of PolyP binding to thrombin). As described herein particular UHRAs are unique since the selectivity of the molecules towards polyP is different in comparison to heparin, especially in vivo. As described herein, numerous UHRA polymers strongly inhibited the polyP pro-coagulant activity in vitro. Four of those UHRAs were selected for further in vivo testing in mouse models of thrombosis and hemostasis. Furthermore, these UHRA polymers were found to have significantly less bleeding as compared with therapeutically equivalent antithrombotic doses of heparin in mouse tail bleeding assays. Accordingly, the polymers described herein may provide alternative antithrombotic agents that target procoagulant anionic polymers (for example polyP), but that have reduced toxicity and bleeding as compared to known anti-thrombotic agents. Furthermore, the polymers described herein have also been shown to bind other anionic polymers, like extracellular nucleic acids, which have also been implicated in thrombosis. The polymers described herein may be used as antithrombotic agents. Furthermore, the polymers described herein may be used in the treatment of any one or more of stroke, acute coronary syndrome, pulmonary embolism, atrial fibrillation, venous or arterial thromboembolism, disseminated intravascular coagulation (DIC), deep-vein thrombosis (DVT), peripheral artery disease, trauma-induced coagulopathy, extracorporeal circulation, cancer-associated thrombosis, sepsis, septic shock, Systemic Inflammatory Response Syndrome (SIRS) and inflammation.

Herein are presented compositions and methods for their use in treatment of stroke, acute coronary syndrome (for example, myocardial infarction (MI) or acute myocardial infarction (AMI)), pulmonary embolism, atrial fibrillation, venous or arterial thromboembolism, disseminated intravascular coagulation (DIC), sepsis, septic shock, SIRS, deep-vein thrombosis (DVT), peripheral artery disease, trauma-induced coagulopathy, extracorporeal circulation, cancer-associated thrombosis and inflammation. Furthermore, the polymers described herein may be used to replace heparin treatment, wherein the subject would also benefit from reduced blood loss (i.e. acute coronary syndrome (i.e. MI or AMI (usually due to non-ST elevation myocardial infarction (NSTEMI), ST elevation myocardial infarction (STEMI) or unstable angina), atrial fibrillation, deep-vein thrombosis (DVT), and pulmonary embolism).

In one aspect, there is provided a method of binding a phosphate containing biological macromolecule, the method includes adding a polymer to a phosphate containing biological macromolecule sample, wherein the polymer comprises: a) a dendritic polyglycerol core having 2-33 randomly distributed tetra-amine groups, wherein the tetra-amines have the following structure

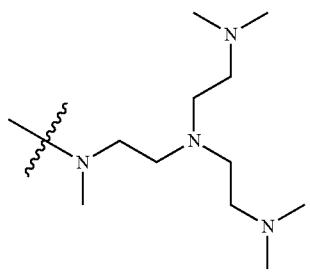 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system.

In another aspect of the invention, there is provided a method of binding a phosphate containing biological macromolecule, the method including administering a polymer to a subject in need of having phosphate containing biological macromolecules bound, wherein the polymer comprises: a) a dendritic polyglycerol core having 5-33 randomly distributed tetra-amine groups, wherein the tetra-amines have the following structure

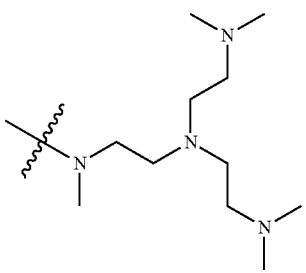 [SMILES: *N(C)CCN(CCN(C)C)CCN(C)C]

and wherein the molecular weight of the polymer in kDa per tetra-amine group does not exceed 4-5 and (b) an outer shell, wherein the outer shell is a hydrophilic polymeric system.

In another aspect of the invention, there is provided a use of a polymer to bind a phosphate containing biological macromolecule, wherein the polymer includes: a) a dendritic polyglycerol core having 2-33 randomly distributed tetra-amine groups, wherein the tetra-amines have the following structure

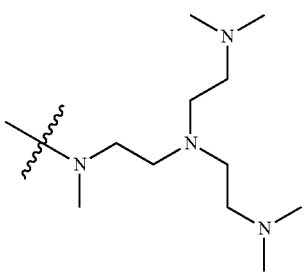 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system.

In another aspect of the invention, there is provided a use of a polymer the polymer includes: a) a dendritic polyglycerol core having 2-33 randomly distributed tetra-amine groups, wherein the tetra-amines have the following structure

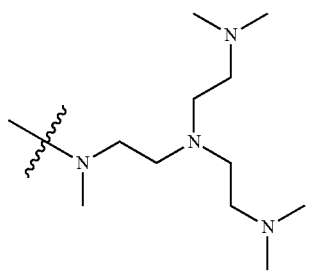 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system, for the treatment of one or more of: stroke; acute coronary syndrome; pulmonary embolism; atrial fibrillation; venous or arterial thromboembolism; disseminated intravascular coagulation (DIC); deep-vein thrombosis (DVT); peripheral artery disease; trauma-induced coagulopathy; extracorporeal circulation; cancer-associated thrombosis; sepsis; septic shock; Systemic Inflammatory Response Syndrome (SIRS); and inflammation.

In another aspect of the invention, there is provided a use of a polymer, wherein the polymer includes: a) a dendritic polyglycerol core having 5-33 randomly distributed tetra-amine groups, wherein the tetra-amines have the following structure

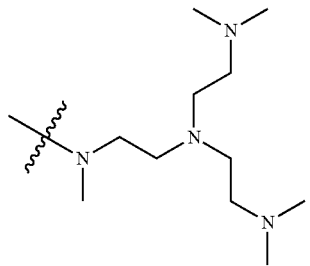 [SMILES: *N(C)CCN(CCN(C)C)CCN(C)C]

and wherein the molecular weight of the polymer in kDa per tetra-amine group does not exceed 4-5 and (b) an outer shell, wherein the outer shell is a hydrophilic polymeric system, in the manufacture of a medicament for inhibiting thrombin binding to polyphosphate in a subject.

In another aspect of the invention, there is provided a use of a polymer, wherein the polymer includes: a) a dendritic polyglycerol core having 5-33 randomly distributed tetra-amine groups, wherein the tetra-amines have the following structure

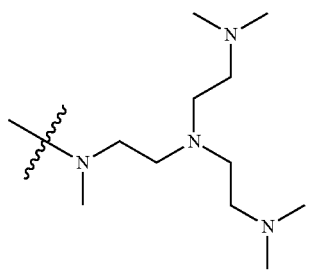 [SMILES: *N(C)CCN(CCN(C)C)CCN(C)C]

and wherein the molecular weight of the polymer in kDa per tetra-amine group does not exceed 4-5 and (b) an outer shell, wherein the outer shell is a hydrophilic polymeric system, in the manufacture of a medicament for treating one or more of: stroke; acute coronary syndrome; pulmonary embolism; atrial fibrillation; venous or arterial thromboembolism; disseminated intravascular coagulation (DIC); deep-vein thrombosis (DVT); peripheral artery disease; trauma-induced coagulopathy; extracorporeal circulation; cancer-associated thrombosis; sepsis; septic shock; Systemic Inflammatory Response Syndrome (SIRS); and inflammation in a subject.

In another aspect of the invention, there is provided a polymer for inhibiting thrombin binding to polyphosphate in a subject, wherein the polymer includes: a) a dendritic polyglycerol core having 2-33 randomly distributed tetra-amine groups, wherein the tetra-amines have the following structure

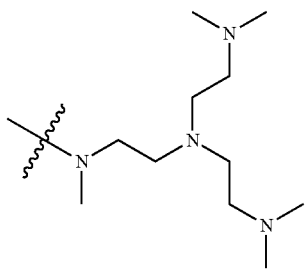 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system.

In another aspect of the invention, there is provided a polymer for the treatment of one or more of: stroke; acute coronary syndrome; pulmonary embolism; atrial fibrillation; venous or arterial thromboembolism; disseminated intravascular coagulation (DIC); deep-vein thrombosis (DVT); peripheral artery disease; trauma-induced coagulopathy; extracorporeal circulation; cancer-associated thrombosis; sepsis; septic shock; Systemic Inflammatory Response Syndrome (SIRS); and inflammation in a subject, wherein the polymer includes: a) a dendritic polyglycerol core having 2-33 randomly distributed tetra-amine groups, wherein the tetra-amines have the following structure

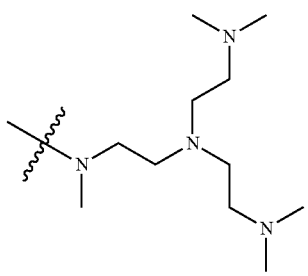 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system.

In another aspect of the invention, there is provided a polymer polymer for use as an antithrombotic agent, wherein the polymer includes: a) a dendritic polyglycerol core having 2-33 randomly distributed tetra-amine groups, wherein the tetra-amines have the following structure

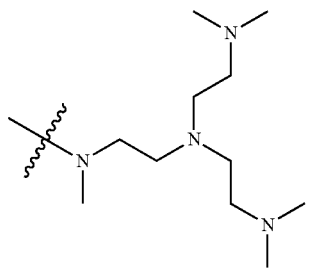 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system.

In another aspect of the invention, there is provided a commercial package including a polymer, wherein the polymer includes: a) a dendritic polyglycerol core having 2-33 randomly distributed tetra-amine groups, wherein the tetra-amines have the following structure

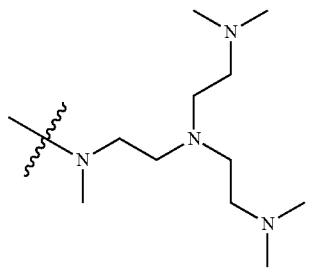 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system, and instructions for use in the treatment of stroke; acute coronary syndrome; pulmonary embolism; atrial fibrillation; venous or arterial thromboembolism; disseminated intravascular coagulation (DIC); deep-vein thrombosis (DVT); peripheral artery disease; trauma-induced coagulopathy; extracorporeal circulation; cancer-associated thrombosis; sepsis; septic shock; Systemic Inflammatory Response Syndrome (SIRS); and inflammation.

In another aspect of the invention, there is provided a commercial package including a polymer wherein the polymer includes: a) a dendritic polyglycerol core having 2-33 randomly distributed tetra-amine groups, wherein the tetra-amines have the following structure

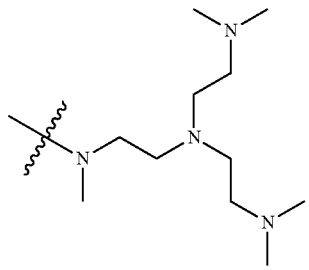 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system, and instructions for use in inhibiting thrombin binding to polyphosphate.

In another aspect of the invention, there is provided a commercial package including a polymer wherein the polymer includes: a) a dendritic polyglycerol core having 2-33 randomly distributed tetra-amine groups, wherein the tetra-amines have the following structure

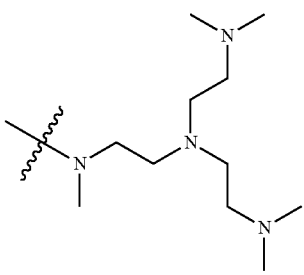 [SMILES: *N(C)CCN(CCN(C)C)CCN(C)C]

and wherein the molecular weight of the polymer in kDa per tetra-amine group does not exceed 4-5; and (b) an outer shell, wherein the outer shell is a hydrophilic polymeric system, and instructions for use as an antithrombotic agent.

The outer shell may be a hydrophilic polymeric system. Such an outer shell may be a pharmaceutically acceptable and biocompatible, especially where a polymer is for administration to a subject or for the purification of or extraction from a biological fluid (for example, blood). The hydrophilic polymeric system may be a polyether or polyalcohol. The polyether or polyalcohol may be a low molecular weight polyglycerol, linear polyglycerol, oligosaccharides, poly(N-isopropylacrylamide) (PNIPAM), polyacrylamide (PAM), poly(2-oxazoline), poly(ethylene glycol), methoxy (polyethylene glycol), poly(ethylene oxide), poly(vinyl alcohol) (PVA), or poly(vinylpyrrolidone) (PVP) or other water soluble polymers or a combination thereof. The hydrophilic polymeric system may be PEG, PEG-OH or PEG-OMe or a combination thereof. The hydrophilic polymeric system may be

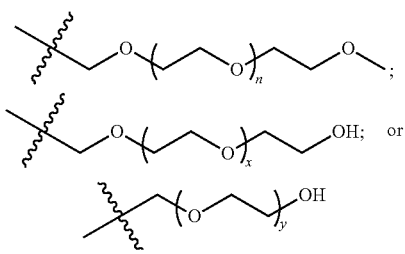

or a combination thereof, wherein n is 0-100, x is 0-100 and y is 0-100. The outer shell may be selected from one or more of:

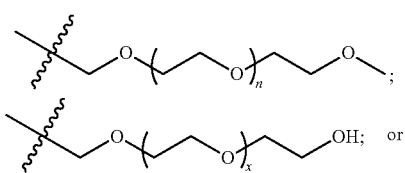

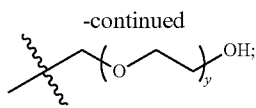

wherein n is 0-100, x is 0-100 and y is 0-100. The outer shell polymer density of a compound may be given as a wt %. The compounds may have PEG by weight in the range 60-75 wt %. The compounds may have PEG by weight in the range 10 to 90 wt %.

n may be an integer between 1 and 100, m may be an integer between 1 and 100 and y may be an integer between 1 and 100. n may be an integer between 1 and 90, m may be an integer between 1 and 90 and y may be an integer between 1 and 90. n may be an integer between 1 and 80, m may be an integer between 1 and 80 and y may be an integer between 1 and 80. n may be an integer between 1 and 70, m may be an integer between 1 and 70 and y may be an integer between 1 and 70. n may be an integer between 1 and 60, m may be an integer between 1 and 60 and y may be an integer between 1 and 60. n may be an integer between 1 and 50, m may be an integer between 1 and 50 and y may be an integer between 1 and 50. n may be an integer between 1 and 40, m may be an integer between 1 and 40 and y may be an integer between 1 and 40. n may be an integer between 1 and 30, m may be an integer between 1 and 30 and y may be an integer between 1 and 30. n may be an integer between 1 and 25, m may be an integer between 1 and 25 and y may be an integer between 1 and 25. n may be an integer between 1 and 20, m may be an integer between 1 and 20 and y may be an integer between 1 and 20. n may be an integer between 1 and 10, m may be an integer between 1 and 10 and y may be an integer between 1 and 10. n may be an integer between 1 and 9, m may be an integer between 1 and 9 and y may be an integer between 1 and 9. n may be an integer between 1 and 8, m may be an integer between 1 and 8 and y may be an integer between 1 and 8. n may be an integer between 1 and 7, m may be an integer between 1 and 7 and y may be an integer between 1 and 7. n may be an integer between 1 and 6, m may be an integer between 1 and 6 and y may be an integer between 1 and 6. n may be an integer between 1 and 5, m may be an integer between 1 and 5 and y may be an integer between 1 and 5. n may be an integer between 3 and 10, m may be an integer between 3 and 10 and y may be an integer between 3 and 10. n may be an integer between 4 and 9, m may be an integer between 4 and 9 and y may be an integer between 4 and 9. n may be an integer between 5 and 8, m may be an integer between 5 and 8 and y may be an integer between 5 and 8.

The binding of the phosphate containing biological macromolecule may result in neutralization. The phosphate containing biological macromolecule may be polyphosphate or a nucleic acid. The phosphate containing biological macromolecule may be polyphosphate. The binding to polyphosphate may disrupt the interaction between thrombin and polyphosphate.

The polyglycerol core may have between 4-50 randomly distributed tetra-amine groups. The polyglycerol core may have between 5-33 randomly distributed tetra-amine groups. The polyglycerol core may have between 7-24 randomly distributed tetra-amine groups. The polyglycerol core may have between 11-24 randomly distributed tetra-amine groups. The polyglycerol core may have between 12-23 randomly distributed tetra-amine groups. The polyglycerol core may have between 7-16 randomly distributed tetra-amine groups. The polyglycerol core may have between 8-16 randomly distributed tetra-amine groups.

The molecular weight of the polymer in kDa per tetra-amine group may be between 0.9 and 4.5. The molecular weight of the polymer in kDa per tetra-amine group may be between 0.5 and 4.5. The molecular weight of the polymer in kDa per tetra-amine group may be between 0.1 and 4.5. The molecular weight of the polymer in kDa per tetra-amine group may be between 0.9 and 4.0. The molecular weight of the polymer in kDa per tetra-amine group may be between 0.8 and 4.0. The molecular weight of the polymer in kDa per tetra-amine group may be between 0.9 and 3.9. The molecular weight of the polymer in kDa per tetra-amine group may be between 0.9 and 3.8. The molecular weight of the polymer in kDa per tetra-amine group may be between 0.9 and 3.7. The molecular weight of the polymer in kDa per tetra-amine group may be between 0.9 and 3.6. The molecular weight of the polymer in kDa per tetra-amine group may be between 0.9 and 3.5. The molecular weight of the polymer in kDa per tetra-amine group may be between 0.9 and 3.4. The molecular weight of the polymer in kDa per tetra-amine group may be between 0.9 and 3.3. The molecular weight of the polymer in kDa per tetra-amine group may be between 0.9 and 3.2. The molecular weight of the polymer in kDa per tetra-amine group may be between 0.9 and 3.1. The molecular weight of the polymer in kDa per tetra-amine group may be between 0.9 and 3.0. The molecular weight of the polymer in kDa per tetra-amine group may be between 0.9 and 2.9. The molecular weight of the polymer in kDa per tetra-amine group may be between 0.9 and 2.8. The molecular weight of the polymer in kDa per tetra-amine group may be between 0.9 and 2.7. The molecular weight of the polymer in kDa per tetra-amine group may be between 0.9 and 2.6. The molecular weight of the polymer in kDa per tetra-amine group may be between 0.9 and 2.5. The molecular weight of the polymer in kDa per tetra-amine group may be between 0.7 and 2.5. The molecular weight of the polymer in kDa per tetra-amine group may be between 0.8 and 2.5. The molecular weight of the polymer in kDa per tetra-amine group may be between 0.9 and 2.4. The molecular weight of the polymer in kDa per tetra-amine group may be between 0.9 and 2.3. The molecular weight of the polymer in kDa per tetra-amine group may be between 0.9 and 2.2. The molecular weight of the polymer in kDa per tetra-amine group may be between 0.9 and 2.1. The molecular weight of the polymer in kDa per tetra-amine group may be between 0.9 and 2.0. The molecular weight of the polymer in kDa per tetra-amine group may be between 0.9 and 1.9. The molecular weight of the polymer in kDa per tetra-amine group may be between 0.9 and 1.8. The molecular weight of the polymer in kDa per tetra-amine group may be between 0.9 and 1.7. The molecular weight of the polymer in kDa per tetra-amine group may be between 0.9 and 1.6. The molecular weight of the polymer in kDa per tetra-amine group may be between 0.9 and 1.5. The molecular weight of the polymer in kDa per tetra-amine group may be between 0.8 and 1.5. The molecular weight of the polymer in kDa per tetra-amine group may be between 0.7 and 1.5. The molecular weight of the polymer in kDa per tetra-amine group may be between 0.9 and 1.4. Alternatively, the molecular weight of the polymer in kDa per tetra-amine may not exceed 3.6.

The polymer may have an $IC_{50}$ (nM) for inhibition of thrombin binding to polyphosphate that is equal to or less than 50 nM. The polymer may have an $IC_{50}$ (nM) for inhibition of thrombin binding to polyphosphate that is equal to or less than 45 nM. The polymer may have an $IC_{50}$ (nM) for inhibition of thrombin binding to polyphosphate that is equal to or less than 40 nM. The polymer may have an $IC_{50}$ (nM) for inhibition of thrombin binding to polyphosphate that is equal to or less than 35 nM. The polymer may have an $IC_{50}$ (nM) for inhibition of thrombin binding to polyphosphate that is equal to or less than 30 nM. The polymer may have an $IC_{50}$ (nM) for inhibition of thrombin binding to polyphosphate that is equal to or less than 25 nM. The polymer may have an $IC_{50}$ (nM) for inhibition of thrombin binding to polyphosphate that is equal to or less than 20 nM. The polymer may have an $IC_{50}$ (nM) for inhibition of thrombin binding to polyphosphate that is equal to or less than 15 nM. The polymer may have an $IC_{50}$ (nM) for inhibition of thrombin binding to polyphosphate that is equal to or less than 10.2 nM. The polymer may have an $IC_{50}$ (nM) for inhibition of thrombin binding to polyphosphate that is equal to or less than 10 nM.

The polyglycerol core may have a degree of branching in the range of about 0.05 to about 0.95. The polyglycerol core may have a degree of branching in the range of about 0.10 to about 0.95. The polyglycerol core may have a degree of branching in the range of about 0.10 to about 0.90. The polyglycerol core may have a degree of branching in the range of about 0.15 to about 0.85. The polyglycerol core may have a degree of branching in the range of about 0.25 to about 0.75. The polyglycerol core may have a degree of branching in the range of about 0.35 to about 0.65. The polyglycerol core may have a degree of branching in the range of about 0.40 to about 0.60. The polyglycerol core may have a degree of branching in the range of about 0.40 to about 0.65.

The polymer may be UHRA-1, UHRA-2, UHRA-5, UHRA-6, UHRA-7, UHRA-8, UHRA-9, UHRA-10, UHRA-11, UHRA-13, UHRA-14 or UHRA-15. The polymer may be UHRA-2, UHRA-5, UHRA-6, UHRA-7, UHRA-8, UHRA-9, UHRA-10, UHRA-11, UHRA-13, UHRA-14 or UHRA-15. The polymer may be UHRA-2, UHRA-5, UHRA-6, UHRA-7, UHRA-8, UHRA-9, UHRA-10, UHRA-11, UHRA-13 or UHRA-14. The polymer may be UHRA-5, UHRA-6, UHRA-7, UHRA-8, UHRA-9, UHRA-10, UHRA-11, UHRA-13 or UHRA-14. The polymer may be UHRA-6, UHRA-7, UHRA-8, UHRA-9, UHRA-10, UHRA-11 or UHRA-14. The polymer may be UHRA-6, UHRA-7, UHRA-8, UHRA-9, UHRA-10 or UHRA-11. The polymer may be UHRA-7, UHRA-8, UHRA-9, UHRA-10 or UHRA-11. The polymer may be UHRA-5, UHRA-2, UHRA-7 or UHRA-11. The polymer may be UHRA-8, UHRA-9, UHRA-10 or UHRA-14. The polymer may be UHRA-8, UHRA-9 or UHRA-10. The polymer may be UHRA-8 or UHRA-10. The polymer may be UHRA-9 or UHRA-10. The polymer may be UHRA-10.

The subject may be administered the polymer to treat stroke, acute coronary syndrome, pulmonary embolism, atrial fibrillation, venous and arterial thromboembolism, disseminated intravascular coagulation (DIC), deep-vein thrombosis (DVT), peripheral artery disease, trauma-induced coagulopathy, extracorporeal circulation, cancer-associated thrombosis, sepsis, septic shock, Systemic Inflammatory Response Syndrome (SIRS), or inflammation. The subject may be administered the polymer to treat stroke, acute coronary syndrome, pulmonary embolism, atrial fibrillation, venous and arterial thromboembolism, disseminated intravascular coagulation (DIC), deep-vein thrombosis (DVT), peripheral artery disease, trauma-induced coagulopathy, extracorporeal circulation or cancer-associated thrombosis. The subject may be administered the polymer to treat stroke, acute coronary syndrome, pulmonary embolism, atrial fibrillation, venous and arterial thromboembolism, disseminated intravascular coagulation (DIC), deep-vein thrombosis (DVT) or peripheral artery disease. The subject may be administered the polymer to treat stroke, acute coronary syndrome, pulmonary embolism, atrial fibrillation, venous and arterial thromboembolism, disseminated intravascular coagulation (DIC) or deep-vein thrombosis (DVT). The subject may be administered the polymer to treat stroke, acute coronary syndrome, pulmonary embolism, atrial fibrillation or venous/arterial thromboembolism. The subject may be administered the polymer to treat stroke, acute coronary syndrome, pulmonary embolism, atrial fibrillation or thromboembolism. The subject may be administered the polymer to treat stroke, acute coronary syndrome or pulmonary embolism, atrial fibrillation or venous/arterial thromboembolism.

The polymer may be immobilized on a support. The polymer may be administered in a dose range of 1 mg/kg to 1000 mg/kg. The polymer may be administered in a dose range of 50-100 mg/kg. The subject may be non-human. The subject may be human. The subject may be a non-human mammal. The subject may be a mouse, a rat, a pig, a dog, a cat, a horse, a sheep, a cattle, a goat or a chicken. The shell polymer may be between about 10 to about 90 wt %.

DETAILED DESCRIPTION

Figure 1:
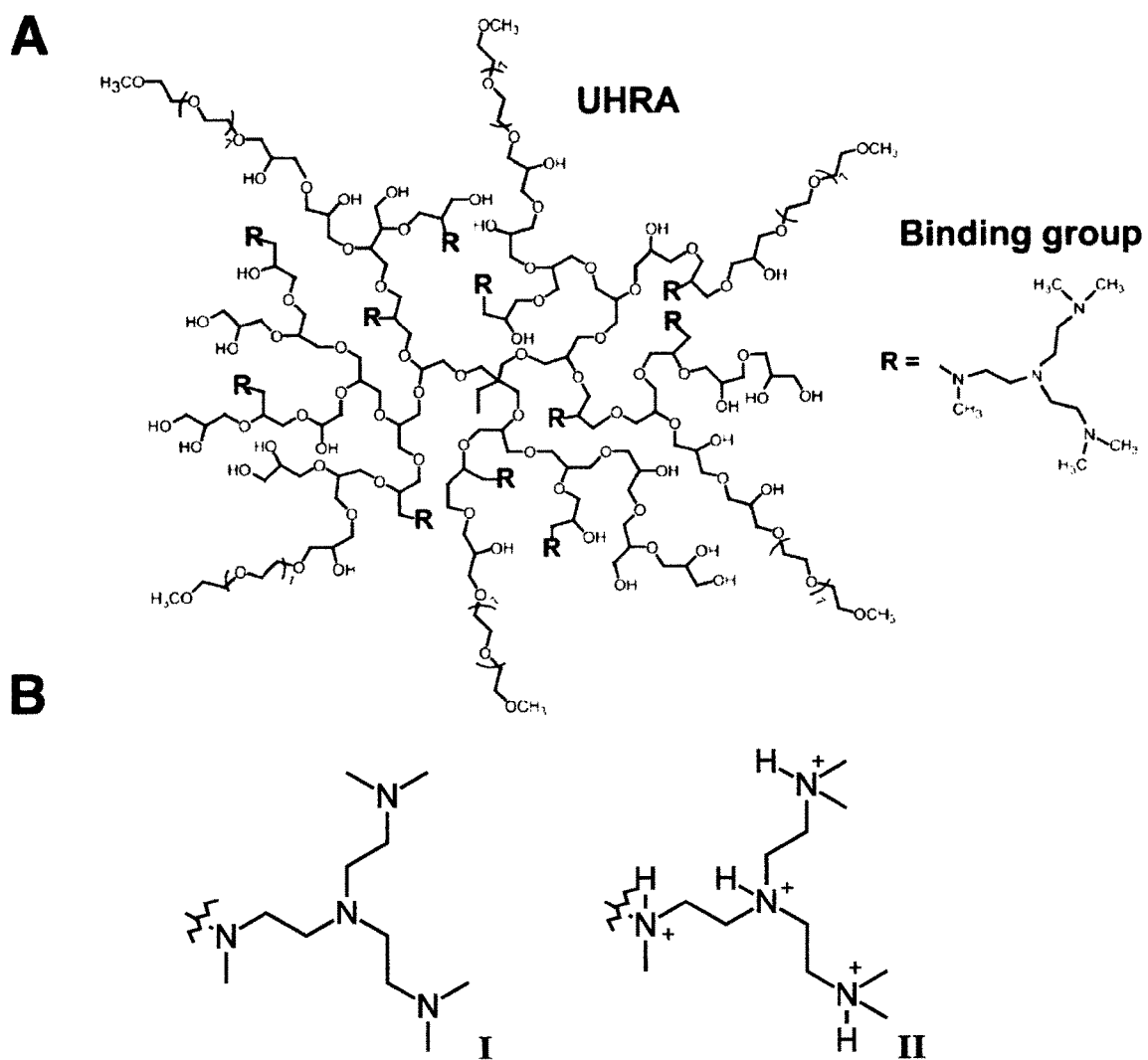
FIG. 1A shows a representative structure of a UHRA scaffold (i.e. UHRA-10), containing a dendritic polyglycerol core bearing the randomly distributed polyP-binding groups (R) and an outer shell of short-chain polyethylene glycols (the molecular weight and number of R groups was varied to generate the other UHRAs). However, it will be appreciated by a person of skill in the art, that the structure shown is not a uniquely defined structure. Based on the way the polymers are synthesized there is some variation in the structure possible.
FIG. 1B shows the binding group (R group) in two formats (I) un-protonated and (II) protonated structure at physiological pH (pH 7.4) when the tertiary amine groups are protonated to provide the cationic binding moiety.

Polyphosphate (polyP) is secreted by activated platelets and has been shown to contribute to thrombosis, suggesting that it could be a novel antithrombotic target. Previously reported polyP inhibitors based on polycationic substances such as polyethylenimine (PEI), polyamidoamine (PAMAM) dendrimers and polymyxin B, while attenuating thrombosis, all have significant toxicity in vivo, likely due to the presence of multiple primary amines responsible for their polyP binding ability. Herein, a novel class of non-toxic polycationic polymers were examined. The polymers were initially designed as Universal Heparin Reversal Agents (UHRAs), but were tested herein for their ability to block polyP procoagulant activity and therefore, their utility as antithrombotic treatments. Several UHRA compounds strongly inhibited polyP procoagulant activity in vitro and four were selected for further examination in mouse models of thrombosis and hemostasis. Compounds UHRA 9 and UHRA 10 reduced arterial thrombosis in mice and were as effective as heparin. In mouse tail bleeding tests, administration of UHRA 9 or UHRA 10 was associated with significantly less bleeding compared to therapeutically equivalent doses of heparin. Thus, these compounds offer a new platform for developing novel antithrombotic agents that target procoagulant anionic polymers like polyP with reduced toxicity and bleeding side effects.

Recently a family of dendritic polymer-based universal heparin reversal agents (UHRA) were developed as synthetic antidotes to all heparin-based anticoagulants (33, 34). These UHRAs were designed by assembling multifunctional cationic groups into the core of a dendritic polymer, which are then shielded from non-specific interactions with blood components using a protective layer of short-chain polyethylene glycol (PEG). The binding of UHRA to anionic heparins is optimized by the arrangement of cationic groups and the size of the polymer scaffold. Specific UHRA compounds showed high binding affinity to various heparins and neutralized their anticoagulant activity while exhibiting excellent blood compatibility and non-toxicity in vivo that is not usually observed with conventional cationic polymers (33).

While the development and synthesis of UHRA compounds allowed the identification of important new heparin reversal agents, we also realized that within the UHRA family of compounds we might find polymer structures that could function as non-toxic polyP inhibitors. The extremely low toxicity, coupled with the ease with which their chemical composition and pharmacological properties can be varied, made the UHRA compounds ideal candidates for testing and developing this novel class of antithrombotic agents targeting polyP. As described herein there was a successful identification of UHRA compounds with high affinity for polyP in vitro, and which also interrupt thrombosis in vivo.

Without wishing to be bound by any particular theory, there can be discussion herein of beliefs or understandings of underlying principles or mechanisms relating to embodiments of the disclosure. It is recognized that regardless of the ultimate correctness of any explanation or hypothesis, an embodiment of the disclosure can nonetheless be operative and useful.

The foregoing and other objects and features of the disclosure will become more apparent from the following detailed description, which proceeds with reference to the accompanying figures.

Further embodiments, forms, features, aspects, benefits, objects, and advantages of the present application shall become apparent from the detailed description and figures provided herewith.

Definitions

A 'nucleic acid molecule' as used herein is meant to be a single- or double-stranded linear polynucleotide containing either deoxyribonucleotides or ribonucleotides that are linked by 3'-5'-phosphodiester bonds.

An 'outer shell' as used herein is meant to be a 'hydrophilic polymeric system'. Such an outer shell would generally be pharmaceutically acceptable and biocompatible, especially where a polymer is for administration to a subject or for the purification of or extraction from a biological fluid (for example, blood). A 'hydrophilic polymeric system' as used herein is meant to encompass most any polyether or polyalcohol. Examples of such polyethers and polyalcohols are low molecular weight polyglycerol, linear polyglycerol, oligosaccharides, poly(N-isopropylacrylamide) (PNIPAM), polyacrylamide (PAM), poly(2-oxazoline), poly(ethylene glycol), methoxy (polyethylene glycol), poly(ethylene oxide), poly(vinyl alcohol) (PVA), or poly(vinylpyrrolidone) (PVP) or other water soluble polymers or a combination thereof. Specific examples may be PEG, PEG-OH and PEG-OMe. Specific examples, may also be

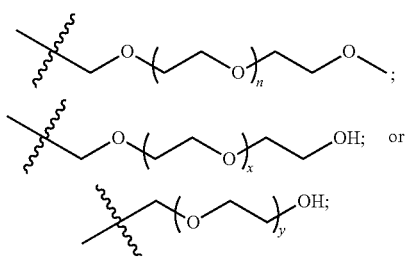

wherein n is 0-100, x is 0-100 and y is 0-100.

The outer shell polymer density of a compound may be given as a wt %. For example, most of the exemplified compounds have PEG by weight in the range 60-75 wt %. However, the useful range may be anywhere from 10 to 90 wt %.

As shown in FIG. 1B, the R group (R) or the binding group may be represented in different ways. Structure I is the actual structure of the binding group, and II is the same structure at physiological pH (pH 7.4) when the tertiary amine groups get protonated giving rise to a cationic molecule. The cationic molecule is able to bind to negatively charged (anionic) molecules or macromolecules.

A 'sample' as used herein is meant to include a representative part of a larger whole, a complete extract or majority portion of the larger whole, a group of samples pooled from a number of sources, wherein the pooled sample may include a complete extract or majority portion thereof, or representative part of a larger whole or combinations thereof. For example, the sample may be used for the extraction of phosphate containing biological macromolecule, wherein the sample is a pooled blood sample.

As used herein 'neutralize' is to counteract the activity or effect of a given entity, in whole or in part. The neutralization, may be reversible and the neutralization may be total (for example, excluding all possible binding partners) or may be partial (for example, excluding one or a few binding partners). For example, neutralization, may result in the blocking one or more particular binding partners to the entity being neutralized or may be specific to one or more binding partners and not bind to the entity being neutralized at all.

As used herein, the term 'treatment' means to treat, prevent, or otherwise ameliorate the symptoms or underlying cause of a disease, syndrome, or condition. Treatment may include administering a therapeutically beneficial pharmaceutical composition, and the timing of such treatment may vary. For instance, treatment may occur prior to the presentation of symptoms, during the onset of symptoms, or after the full development of symptoms. Treatment may include acute treatment regimens, for instance only one or a few doses. Treatment may include chronic treatment regimens, for instance regular or irregular repeated doses over a longer term, which may include repeated doses over the entire lifetime of a subject. Treatment may include administering a therapeutically beneficial pharmaceutical composition to a subject with a confirmed diagnosis of having a disease, syndrome, or condition. Treatment may include administering a therapeutically beneficial pharmaceutical composition to a subject who is suspected of having a disease, syndrome, or condition. Treatment may include administering a therapeutically beneficial pharmaceutical composition to a subject at risk of having a disease, syndrome, or condition.

Compounds as described herein may be in the free form or in the form of a salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenyipropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, catheter, graft, prosthesis, stent, etc. Also, implants may be devised which are intended to contain and release such compounds or compositions. An example would be an implant made of a polymeric material adapted to release the compound over a period of time. Furthermore, the compounds described herein may be immobilized on a 'support' to be used to filter a biological or other fluid, or to extract a phosphate containing biological macromolecule or to extract an anionic biological macromolecule.

An 'effective amount' of a pharmaceutical composition as described herein includes a therapeutically effective amount or a prophylactically effective amount. A 'therapeutically effective amount' refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A 'prophylactically effective amount' refers to an amount effective, at dosages and for periods of time necessary, to achieve the desired prophylactic result, such as reduced thrombosis, increased life span, increased life expectancy or prevention of the progression of disease. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: stroke, acute coronary syndrome (for example, myocardial infarction (MI) or acute myocardial infarction (AMI)), pulmonary embolism, atrial fibrillation, venous or arterial thromboembolism, disseminated intravascular coagulation (DIC), sepsis, septic shock, Systemic Inflammatory Response Syndrome (SIRS), deep-vein thrombosis (DVT), peripheral artery disease, trauma-induced coagulopathy, extracorporeal circulation, cancer-associated thrombosis and inflammation. For example, compounds and all their different forms as described herein may be used as neoadjuvant (prior), adjunctive (during), and/or adjuvant (after) therapy with surgery or other therapies.

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Toxicity may be evaluated by examining a particular compound's or composition's specificity across cell lines. Animal studies may be used to provide an indication if the compound has any effects on other tissues.

Compounds as described herein may be administered to a subject. As used herein, a 'subject' may be a human, non-human primate, rat, mouse, cow, horse, pig, sheep, goat, dog, cat, etc. The subject may be suspected of having or at risk for having one or more of stroke, acute coronary syndrome (for example, myocardial infarction (MI) or acute myocardial infarction (AMI)), pulmonary embolism, atrial fibrillation, venous or arterial thromboembolism, disseminated intravascular coagulation (DIC), sepsis, septic shock, Systemic Inflammatory Response Syndrome (SIRS), deep-vein thrombosis (DVT), peripheral artery disease, trauma-induced coagulopathy, extracorporeal circulation, cancer-associated thrombosis and inflammation.

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

Materials and Methods

Chemicals were from Sigma-Aldrich™ and used without further purification unless mentioned. Glycidol was purified by distillation under reduced pressure before use and stored over molecular sieves at 4° C. $^1$H nuclear magnetic resonance spectra were acquired in deuterium oxide on a Bruker Avance AV-300 spectrometer. Absolute molecular weights of the polymers were determined by Gel Permeation Chromatography (GPC) on a Waters 2695™ separation module fitted with a DAWN EOS multiangle laser light scattering (MALLS) detector coupled with Optilab DSP™ refractive index detector, both from Wyatt Technology™. GPC analysis was performed using Waters™ ultrahydrogel columns (guard, linear and 120) and 0.1 M $NaNO_3$ (10 mM phosphate buffer) as the mobile phase.

Synthesis of UHRA 10

The polymer scaffolds of this family of UHRA compounds were synthesized by anionic ring-opening polymerization of glycidol and a-methoxy-v-epoxy polyethylene glycol (mPEG-400), which were then postfunctionalized to introduce positively charged groups based on branched tertiary amines. Detailed synthetic methods are provided below and described in publications (33, 34).

In the first step, a HPG-PEG polymer was synthesized as follows: A three-necked round bottomed flask was cooled under vacuum and filled with argon. To this, 1,1,1-tris (hydroxymethyl)propane (TMP, 0.240 g) and potassium methylate (25 wt % solution in methanol, 0.220 mL) were added and stirred for 30 minutes. Methanol was removed under vacuum for 4 hours. The flask was heated to 95° C. and glycidol (2.5 mL) was added over a period of 15 hours. After complete addition of monomer, the reaction mixture was stirred for additional 3 hours. mPEG-epoxide400 (9 mL) was added over a period of 12 hours. The reaction mixture was stirred for additional 4 hours. The polymer was dissolved in methanol, and twice precipitated from diethyl ether. The polymer was dissolved in water and dialyzed against water using MWCO-1000 membrane for 3 days with periodic changes in water. Yield: 80%. $^1$H NMR (CDCl$_3$, 300 MHz): δ ppm 3.37 (—OCH$_3$ from PEG), 3.4-3.95 (main chain protons from HPG and PEG). PEG content: 35 mol %; Polyglycerol: 65 mol %; GPC-MALLS (0.1 M NaNO$_3$): Mn 10000; Mw/Mn 1.7.

The HPG-PEG-10 kDa precursor polymer (2.4 g) was then dissolved in 25 mL of pyridine. To this, p-toluenesulfonyl chloride (8 g) was added and stirred at room temperature for 24 hours. Pyridine was removed by rotary evaporation; the polymer was dissolved in 0.1 N HCl and dialyzed overnight. The HPG-PEG-tosylate was isolated by freeze drying. The HPG-PEG-tosylate (2.8 g) and tris (2-aminoethylamine) (8 mL) were dissolved in 1,4-dioxane (25 mL) and refluxed for 24 hours. Dioxane was removed under vacuum and the polymer was dissolved in minimum amount of methanol and precipitated twice from diethyl ether. The polymer was then dissolved in water and dialyzed against water using MWCO-1000 membrane for 2 days. The resulting polymer solution was added to a mixture of formaldehyde (6 mL) and formic acid (6 mL) at 0° C. The reaction mixture was refluxed overnight. After cooling to room temperature, the pH of the solution was adjusted to 10 using NaOH and the polymer was extracted with dichloromethane. Dichloromethane was removed under vacuum; the polymer dissolved in distilled water and dialyzed against water using MWCO-1000 membrane with frequent changes in water for 2 days. The number of binding groups in UHRA 10 (by conductometric titration) was calculated to be 11. $^1$H NMR (CDCl$_3$, 300 MHz): δ ppm 2.27 (—NCH$_3$), 2.4-2.7 (—N—CH$_2$—), 3.38 (—OCH$_3$ from PEG), 3.4-3.95 (main chain protons from HPG and PEG).

The other UHRAs were synthesized using a similar procedure as outline above. HPG-PEG polymer having respective molecular weight was synthesized in the first step and the amount of reagents in the post-functionalization step was varied to obtain different number of binding groups on the UHRAs. The molecular weight and number of binding groups of different UHRAs are given in TABLE 2. The structure of the other UHRAs is similar to the one shown in FIG. 1A, with differences in the number of glycerol units of the polymer (—O—CH$_2$—CH(O)—CH$_2$—O—), PEG units and the number of R groups. The 'R' groups are distributed randomly within the polymeric structure. The number of glycerol and PEG units per UHRA increases with molecular weight of the construct.

All the UHRAs were synthesized using a similar procedure as that described for UHRA 10 in the main description above. In the first step, HPG-PEG polymer of the respective molecular weight was prepared and the proportion of the reagents in the post functionalization step was varied to introduce different number of polyP-binding groups (R) on UHRAs. The characteristics of the UHRAs are given below. The number of binding groups on UHRAs was determined by conductometric titration.

Characterization of UHRAs

UHRA 1: HPG-PEG polymer: PEG content: 35 mol %; Polyglycerol: 65 mol %; GPC-MALLS (0.1 M NaNO$_3$): Mn 116000 g/mol; Mw/Mn 1.2. Number of polyP-binding groups per polymer: 33.

UHRA 2: HPG-PEG polymer: PEG content: 33 mol %; Polyglycerol: 67 mol %; GPC-MALLS (0.1 M NaNO$_3$): Mn 48000 g/mol; Mw/Mn 1.45. Number of polyP-binding groups per polymer: 18.

UHRAs 3 to 8: HPG-PEG polymer: PEG content: 35 mol %; Polyglycerol: 65 mol %; GPC-MALLS (0.1 M NaNO$_3$): Mn 23000 g/mol; Mw/Mn 1.52. The number of polyP-binding groups per polymer was 4, 5, 11, 16, 20 and 24 for UHRAs 3, 4, 5, 6, 7, and 8 respectively.

UHRA 9: HPG-PEG polymer: PEG content: 32 mol %; Polyglycerol: 68 mol %; GPC-MALLS (0.1 M NaNO$_3$): Mn 16000 g/mol; Mw/Mn 1.8. Number of polyP-binding groups per polymer: 16.

UHRA 11: HPG-PEG polymer: PEG content: 34 mol %; Polyglycerol: 66 mol %; GPC-MALLS (0.1 M NaNO$_3$): Mn 9400 g/mol; Mw/Mn 1.34. Number of polyP-binding groups per polymer: 8.

UHRAs 12, 13 and 14: HPG-PEG polymer: PEG content: 28 mol %; Polyglycerol: 72 mol %; GPC-MALLS (0.1 M NaNO$_3$): Mn 10000 g/mol; Mw/Mn 1.41. Number of polyP-binding groups per polymer was 2, 5 and 7 respectively in UHRA 12, 13 and 14.

UHRAs 15 and 16: HPG-PEG polymer: PEG content: 32 mol %; Polyglycerol: 68 mol %; GPC-MALLS (0.1 M NaNO$_3$): Mn 4900 g/mol; Mw/Mn 1.4. Number of polyP-binding groups per polymer was 2 and 1 respectively in UHRA 15 and UHRA 16.

In Vitro Studies

UHRA Biocompatibility Studies

Blood from healthy consented donors was either collected into 3.8% sodium citrate tube with a blood/anticoagulant ratio of 9:1 or serum tube at Centre for Blood Research, University of British Columbia. The protocol was approved by the University of British Columbia clinical ethical committee and written consent was obtained from each individual donor. Platelet-rich plasma (PRP) was prepared by centrifuging citrated whole blood samples at 150×g for 10 min in an Allegra X-22R™ Centrifuge (Beckman Coulter™, Canada). Serum was prepared by centrifuging the blood collected in serum tube at 1200×g for 30 min one hour after blood collection.

Platelet Activation

The level of platelet activation after exposure to polyP inhibitors was quantified by flow cytometry. Ninety microliters of platelet rich plasma (PRP) was incubated at 37° C. with 10 µL of either 10 mg/mL or 20 mg/mL of UHRA, protamine or PEI stock solution (final polymer concentration 1 mg/mL and 2 mg/mL respectively) in PBS. After 1 h, aliquots of the incubation mixtures were removed for assessment of the platelet activation state. Five microliters of post-incubation platelet/polymer mixture, diluted in PBS buffer, was incubated for 20 minutes in the dark with 5 µL of phycoerythrin (PE)-labeled monoclonal anti-CD62P-PE (Immunotech™, Catalog No. PN IM1759U, CLB-Thromb/6 clone and Mouse IgG1 isotype). The samples were then stopped with 0.3 mL of phosphate-buffered saline solution. The level of platelet activation was analyzed in a BD FACSCanto II flow cytometer (Becton Dickinson™) by gating platelets specific events based on their forward scattering profile (size of individual platelet). Activation of platelets was expressed as the percentage of platelet activation marker CD62-PE fluorescence detected in the 10,000 total events counted. Bovine thrombin (1 IU/mL, Sigma) was used as the positive control, and PE-conjugated goat anti-mouse IgG polyclonal antibodies (Immunotech™) were used as the non-specific binding control. PRP from three different donors was used for the analysis and each sample was run in duplicates, the average values (±SD) are reported.

Complement Activation

The level of complement activation after exposure to polyP inhibitors was measured by $CH_{50}$ sheep erythrocyte complement lysis assay in human serum. Stock solutions of UHRA, PEI and protamine at concentrations of 10 mg/mL and 20 mg/mL were prepared in PBS. Ten microliters of the stock solution was mixed with 90 µL of GVB2+ buffer (0.1% gelatin, 5 mM Veronal, 145 mM NaCl, 0.025% $NaN_3$ with 0.15 mM $CaCl_2$ and 0.5 mM $MgCl_2$, pH 7.3, CompTech™) diluted human serum for 1 hour at 37° C. (final polymer concentration of 1 mg/mL or 2 mg/mL). Heat-aggregated human IgG (1 mg/mL) and PBS were used as positive and negative controls, respectively. After 1 hour, 60 µL of post-incubation serum/polymer mixture was diluted by the addition of 120 µL of GVB2+ buffer. Seventy five microliters of GVB2+ diluted serum/UHRA or serum/protamine mixture was incubated for 1 h at 37° C. with 75 µL of Ab-sensitized sheep erythrocyte (CompTech). The reaction was stopped by addition of 300 µL cold GVB-EDTA to each sample. Intact Ab-sensitized sheep erythrocytes were then spun down at 8000 rpm for 3 min and the supernatants were sampled. Percentage sheep erythrocyte lysis was calculated using average absorbance values as follows: % lysis=($Abs_{540}$, test sample−$Abs_{540}$, blank)/($Abs_{540}$, 100% lysis−$Abs_{540}$, blank)×100. Percentage of complement activated (consumed) by the UHRA or protamine sulfate was expressed as: 100−% lysis.

Inhibition of Thrombin Binding to PolyP

Streptavidin coated 96 well plates (Corning™) were incubated with 20 µM biotinylated polyP (monomer concentration, prepared as published previously (29)) diluted in 50 mM Tris-HCl pH 7.4, 1% BSA, 0.05% $NaN_3$, and 0.05% Tween 20 for 3 hours at room temperature. The wells were then washed with 1 M LiCl and water and incubated with 40 nM bovine α-thrombin (Enzyme Research Laboratories™) plus varying concentrations of UHRA inhibitors in 20 mM Hepes NaOH pH 7.4, 50 mM NaCl, 1.4 mM $CaCl_2$, 0.5 mM $MgCl_2$, 0.1% BSA, 0.05% Tween-20, 0.05% $NaN_3$ for 1 hour at room temperature. After washing with 20 mM Hepes NaOH pH 7.4, 0.05% Tween-20, 0.05% $NaN_3$, the amount of thrombin bound to polyP was quantified by monitoring the rate of cleavage of 400 µM Sar-Pro-Arg-p-nitroanilide (Bachem™) in 20 mM Hepes NaOH pH 7.4, 0.05% $NaN_3$ by measuring $A_{405}$ every 30 seconds for 20 minutes at room temperature in a SpectraMax™ Plate Reader (Molecular Devices™)

Plasma Clotting Assays

Plasma clotting times were quantified at 37° C. using a STart4™ coagulometer (Diagnostica Stago™). All clotting assays used final concentrations of 33% pooled normal plasma (George King Bio-Medical™), 25 µM liposomes (70:30 ratio of phosphatidylcholine to phosphatidylserine), 41.7 mM imidazole pH 7.0 and 8.33 mM $CaCl_2$. The clotting assays were initiated by mixing the activator (polyP or polyguanylic acid) with inhibitor, liposomes, and pre-warmed plasma for 3 minutes at 37° C. and clotting was initiated by the addition of prewarmed $CaCl_2$. Activator concentrations of 10 µM long-chain polyP and 25 µg/mL polyguanylic acid (RNA) were chosen to give 60-80 second clotting times in the absence of added inhibitors.

Plasma Clot Formation and Lysis by Turbidity Analysis

Blood from healthy consented donors was collected by venipuncture under a protocol approved by the University of British Columbia clinical ethical committee and written consent was obtained from each individual donor. Platelet-poor plasma (PPP) was prepared by centrifuging citrated whole blood samples at 1000×g for 15 minutes. All plasma clotting and lysis experiments were performed in a clear flat-bottomed 96-well microplate (Costar™) at 37° C. Turbidimetric plasma clotting assays were performed with PPP obtained from three different donors (N=3).

Clotting was initiated in 85 µL of diluted platelet-poor plasma (PPP) mixed with 5 µL of buffer, protamine sulphate or UHRA 8 (dilution 1:20), by the addition of 5 µL of recombinant tissue factor (Innovin™ (1:10,000) and 5 µL of CaCl2 (20 mM). Clot formation was monitored by the changes in absorbance at 405 nm every 30 seconds on a Spectramax VMAX™ plate reader (Molecular Devices™), for 2 hours. Clotting of PPP by recalcification was performed in a similar way as described above in the absence of tissue factor. UHRA 8 or protamine concentrations were as shown. Clotting parameters such as lag time and maximum absorbance (MaxAbs™) were calculated. Lag time is considered as the time point when an exponential increase in absorbance was observed due to protofibril formation. MaxAbs™ is the absorbance at which at least 5 readings were identical (plateau phase, corrected for the lag time).

The lysis of tissue factor-induced plasma clots formed in presence of UHRA 8 or PS exposed to exogenous tissue plasminogen activator (t-PA) was monitored by the microplate turbidimetric assay. Clot lysis experiments were performed in normal control pooled plasma collected from 20 donors (Affinity Biologicals™). Diluted plasma (85 µL) spiked with the UHRA 8 or protamine (dilution 1:10), 5 µL of recombinant tissue factor (Innovin™ (1:10,000)), 5 µL of t-PA (25 ng/mL) and 5 µL of CaCl2 (20 mM) was added to microplate wells. All concentrations are final. The changes in optical density at 405 nm was monitored every 30 seconds for 30 minutes (clot formation), and then every 1 minute thereafter up to 300 minutes at 37° C. Clot lysis half time (CLT50) was defined as the mid-point of the lysis curve excluding the plateau phase and the clear transition. The area under the clot lysis curve is a measure of clot formation time, clot density and lysis potential was calculated by applying trapezoid rule to curve points generated after baseline (lowest absorbance value) subtraction. All analysis was done with GraphPad™ prism 6.0.

Isothermal Titration Calorimetry (ITC)

Binding studies were performed using a VP-ITC microcalorimeter from Microcal, Inc.™ (Northampton, Mass.) with a cell volume of 1.4 mL at 298K. PolyP (PolyP$_{75}$) and UHRA solutions used for titrations were prepared in 10 mM phosphate buffered saline (0.137 M NaCl, pH 7.4). Samples were filtered using 0.2 µm filters and degassed prior to addition. Injections of 10 µl of UHRA (300 µM) solution were performed from a computer controlled microsyringe at an interval of 5 minutes into 5 µM (estimated polymer concentration based on average polymer size of 75 phosphates) polyP solution in the cell. The heats of dilution from titrations of UHRA solution into buffer only (without polyP) were subtracted from the heats obtained from titrations of UHRA solution into polyP solution to obtain net binding heats. All the experiments were carried out in duplicate. Raw ITC data of UHRA binding to polyP was analyzed with Origin™ software from Microcal, Inc.™ (Northampton, Mass.). The one-site binding model was used to fit the isotherms by a nonlinear least-squares analysis.

Scanning Electron Microscopy of Fibrin and Whole Blood Clots

The morphology of clots formed in presence of UHRA and protamine was determined by scanning electron microscopy (SEM) analysis. All samples for SEM were randomly coded and blinded to the individual performing imaging and analysis to avoid bias. Fibrin clots were formed in sterile round-bottomed 5 mL polypropylene tubes (BD Falcon) by mixing purified human fibrinogen (200 µL, 3 mg/mL) in 20 mM HEPES (pH 7.4 and 150 mM NaCl) with 2.5 NIHU/mL thrombin and 3 mM CaCl2 and UHRA or protamine (in HEPES buffer) (0-500 µg/mL). All concentrations are final. Control clot was prepared in the absence of UHRA or protamine. After incubating the solution for 1 hour at 37° C., clots were immediately fixed using karnovsky fixative (2.5% glutaraldehyde and 4% formaldehyde) and repeatedly washed with 0.1 M sodium cacodylate buffer (pH=7.4) followed by post-fixation with 1% v/v osmium tetroxide. The samples were washed three times with distilled water and then dehydrated with gradient ethanol series (20-95% v/v). Clots were then critical point-dried with $CO_2$ in a Tousimis-Autosamdri 815B™ critical point dryer, mounted onto stubs, and gold sputter-coated for SEM examination using Hitachi S-4700™ field emission scanning electron microscope at 5,000× (shown as 5×), 10,000× (shown as 10×) and 25,000× (shown as 25×) magnifications. Images of two different areas of each clot were captured. Fiber diameters of all clots were measured with image analysis software package ImageJ™ (National Institutes of Health, USA). Fiber diameter (n=30) from 8 separate areas of each clot was measured and used for calculating the average fiber size formed.

Whole blood clots were also prepared in 5 mL polypropylene tubes (BD Falcon) by recalcifying 180 µL of whole blood with 20 µL of 11.1 mM CaCl2 (final) in the absence or presence of UHRA/protamine in 20 mM HEPES, pH 7.4, 150 mM NaCl at 37° C. Whole blood clots were then carefully processed for SEM imaging as described for fibrin clots.

Nucleic Acid Coagulation Assays

Blood was collected from healthy consented donors into 3.8% sodium citrate tube with a blood/anticoagulant ratio of 9:1 at the Centre for Blood Research, University of British Columbia. Nucleic acid was isolated from blood using QIAamp™ DNA blood mini kit. The integrity of the isolated DNA was evaluated by performing gel electrophoresis. The concentration of isolated nucleic acid was determined using NanoDrop™ spectrophotometer.

To assess the neutralization of prothrombotic action of nucleic acid by UHRA-8, we performed thromboelastography experiments using Thromboelastograph Hemostasis System 5000™ (TEG) from Haemoscope Corporation™. In this study, whole blood was mixed with nucleic acid to get a final concentration of 10 µg/mL. UHRA-8 solution was prepared in PBS (10 mM phosphate and 150 mM NaCl). 360 µL of whole blood spiked with nucleic acid was then mixed with 40 µl of UHRA (1:10 dilution, final). Then 340 µL of the sample was transferred into the TEG cup and the coagulation analysis was initiated by re-calcifying citrated blood with 20 µL of 0.2M calcium chloride solution. PBS mixed with whole blood was used as control for the experiment.

In Vivo Studies

Efficacy of UHRAs in Animal Models of Thrombosis

Animals

Male C57BL/6 mice were obtained from Harlan Laboratories™. All animal procedures were approved by the Institutional Animal Care and Use Committee at the University of Illinois at Urbana-Champaign.

$FeCl_3$-Induced Thrombosis in Mouse Carotid Arteries.

Mice were anesthetized using an inhaled mixture of isoflurane and oxygen, and UHRA compounds diluted in sterile normal saline were injected retro-orbitally. The left carotid artery was exposed via a midline cervical incision and blunt dissection, and blood flow monitored with a Doppler vascular flow probe (Transonic™, 0.5 PSB) connected to a perivascular flow meter (Transonic™, TS420™). To induce thrombosis, two pieces of 1×2 mm filter paper (Whatman™ GB003™) saturated with freshly prepared 5% anhydrous $FeCl_3$ in 0.9% saline were applied to the deep and superficial surfaces of the artery. After 5 minutes, the filter papers were removed and the vessel irrigated with saline. Blood flow was monitored from $FeCl_3$ application for 30 minutes or until occlusion, defined as no detectable flow for one minute. After the experiment ended, mice were euthanatized by cervical dislocation while still under anesthesia. Flow data were interpreted with LabScribe2 (iWorx Systems™). Statistical analyses were performed using GraphPad Prism 5™.

Laser-Induced Thrombosis in Mouse Cremaster Arterioles

Mice were anesthetized with an intraperitoneal injection of 125 mg/kg ketamine, 12.5 mg/kg xylazine, and 0.25 mg/kg atropine sulfate. Approximately 10 minutes prior to imaging, fluorescent antibodies against platelets and fibrin were injected via the jugular vein along with either UHRA compounds or saline. Platelets were labeled with a fluorescent antibody recognizing the GPIbβ subunit of the murine GPIb-V-IX complex (rat antibody X649, conjugated to DyLight649, Emfret Analytics™). Fibrin was labeled with mouse anti-human fibrin antibody clone 59D8 purified from ascites fluid (a generous gift from Hartmut Weiler) with Protein A/G resin (Thermo Scientific™) and labeled with an Alexa Fluor 488™ protein labeling kit according to manufacturer's instructions (Invitrogen™). Anesthetized mice were placed on an intravital microscopy tray and the cremaster muscle was exteriorized through an incision made in the scrotum. The testis and surrounding cremaster muscle were prepared for microscopy by stretching and pinning the tissue onto a custom-made intravital microscopy stage. The cremaster preparation was superfused with 37° C. sterile 0.9% saline throughout the experiment. Brightfield and fluorescent images of arterioles were acquired with a Zeiss Axioplan™ microscope equipped with a Lumencore 4-LED light engine, a 20× water immersion lens (Zeiss W-Plan APOCHROMAT 20×/1.0 NA™), and a Rolera™ em-c² EMCCD Camera (Q-Imaging™). Endothelial injury to the vascular wall of 50-70 μm diameter arterioles that resulted in thrombus formation was effected by the use of a 532 nm pulsed-laser system integrated with the image capture and analysis software (VIVO Imaging System with Ablate! Photomanipulation Module™, Intelligent Imaging Innovations™). Fluorescent and brightfield images were captured for 2 minutes following injury. Fluorescence images were acquired continuously, platelet fluorescence was imaged with a Cy-5 filter and 15 ms exposure, and fibrin was imaged with a fluorescein filter set and 10 ms exposure. Brightfield images were captured with a 10 ms exposure periodically (1 image every 100 captures). Up to 6 injuries were made per mouse with subsequent injuries occurring upstream of previous ones.

Image Analysis of Fluorescent Platelet and Fibrin Accumulation

Integrated fluorescence intensity was calculated with Slidebook 5.5™ (Intelligent Imaging Innovations™) as has been published previously (17). For each injury, a rectangular area was defined upstream of the injury site including both the vessel and the surrounding tissue. The average maximal values for the Cy-5 (X649, platelets) and fluorescein (59D8-Alexa Fluor 488™, fibrin) channels were used as the threshold values to create masks for both platelet and fibrin accumulation. For viewing purposes, the fluorescent pixels in FIGS. 3 and 4 (panels A-E) were binarized (value set to 1) if they exceeded the threshold. To determine the integrated fluorescence intensity for platelets and fibrin, only pixels above this threshold were used in data analysis (but were not binarized). In addition, a small rectangular area was defined completely within the vessel upstream of the injury to serve as a background measurement. Integrated fluorescence intensity at each time point was calculated as (Sum Intensity of the Mask−[Background Intensity*Area of the Mask in Pixels]). Statistical analysis was done by plotting the area under the curve (total fluorescence intensity) for each injury in a given condition and comparing the median values using the Mann-Whitney test. All statistical tests were done using GraphPad Prism 5.0™.

Mouse Tail Bleeding Assay

Mice were anesthetized with an inhaled mixture of isoflurane and oxygen and placed on a heated surgical tray. UHRA compound, heparin, or saline alone was injected retro-orbitally and the tail tip was immersed in a 15 mL Falcon™ tube filled with PBS warmed to 37° C. for 5 minutes. After 5 minutes the distal 2-4 mm of tail was transected with a new razor blade and immediately re-immersed in the warm PBS for 10 minutes. Bleeding time was measured with a stopwatch for the entire 10 minutes. After 10 minutes, the tail was removed from the PBS and the mouse was euthanatized by cervical dislocation. The blood samples were then pelleted at 500×g for 10 minutes at room temperature and the pellet was resuspended in 5 mL of Drabkin's Reagent (Sigma™) and incubated at room temperature for 15 minutes. The amount of hemoglobin lost was quantified by comparing the absorbance of the samples at 540 nm to a standard curve of bovine hemoglobin in Drabkin's reagent.

Assessment of UHRA Toxicity in Animals

Lack of UHRA 10 toxicity in vivo, wherein dose tolerance of UHRA was examined in mice by the administration of 100 mg/kg, 200 mg/kg of UHRA-10 or saline control. Female Balb/C mice (6-8 weeks, 20-26 g) that were individually weighed and were divided into groups (n=3 for each group) for each dose and injected intravenously (via tail vein) with UHRA-10 (100 mg/kg or 200 mg/kg) using a 28 G needle (injection volume was 200 μL/20 g mouse), wherein the mice were housed in cages and monitored for signs of acute toxicity over a period of 14 days after injection and body weights of individual mice were recorded prior to injection and three times per week thereafter. On day 14, mice were euthanized by $CO_2$ asphyxiation, blood (50 μL) was collected from each mouse on the final day and necropsy was performed on all animals. Serum samples were analyzed for lactate dehydrogenase (LDH) activity using the IDTox™ lactate dehydrogenase enzyme assay kit (ID Labs Inc.™). Upon euthanasia of the mice on day 14, whole liver, spleen and both the kidneys were removed from each animal. The tissues were washed in ice cold saline to remove blood and immediately fixed in 10% neutral buffered formalin and processed, embedded in paraffin, sectioned, and stained with hematoxylin and eosin (H&E). Histopathological analysis (H&E staining) on tissue sections after administration of 200 mg/kg UHRA-10 also did not show any toxicity effects such as tissue damage, cell necrosis or inflammation.

Biodistribution Studies in Mice Following i.v. and s.c. Administration

Radiolabelling of the UHRA-10 was performed by partial conversion of the hydroxyl groups to methoxide groups using tritiated methyl iodide. Two hundred milligrams of UHRA-10 was dissolved in 2 mL of anhydrous DMSO and approximately 5% of the hydroxyl groups were deprotonated using sodium hydride. A calculated amount of tritiated methyl iodide (toluene solution) dissolved in DMSO was added to this solution so as to achieve methylation of 1% of the hydroxyl groups. The reaction mixture was stirred at room temperature for 15 h, 10 mL of water was added and the labelled UHRA-10 was purified by dialysis against water using MWCO 1000 dialysis membrane until the dialyzate contained low amounts of radioactivity, this took approximately 48 h. The UHRA-10 solution was then filtered through 0.2 mm syringe filter and the polymer weight was determined from the total volume and the polymer concentration from a known volume of the solution after freeze-drying. The polymer solution for the animal study was prepared by the addition of appropriate amount of NaCl and water to achieve the desired osmolarity and the specific activity was measured by scintillation counting.

Biodistribution studies were performed using tritiated UHRA-10. Female Balb/C mice (6-8 weeks, 17-23 g) were used for the entire study. Animals for each route of administration were divided into 9 groups (n=3) and injected intravenously (bolus) via lateral tail vein or subcutaneously with UHRA-10 (concentration 2 mg/mL) at the prescribed dose of 20 mg/kg. The injected volume was 200 μL per 20 g mouse. Mice were terminated at different time points (5 min, 0.5, 1, 2, 4, 24, 48, 72 h) by CO2 inhalation and blood was collected by cardiac puncture. Plasma was separated by centrifuging the blood samples at 2500 rpm for 15 min. Aliquots of plasma were analyzed for their radioactivity by scintillation counting.

The group of mice for the 72 h time point was housed in metabolic cage and urine and feces were collected as pooled samples at different time points. Aliquots of urine were analyzed for radioactivity by scintillation counting. Feces were made into 10% homogenate into a known amount of water and the radioactivity was measured by scintillation counting.

Upon termination, major organs such as liver, spleen, kidney, heart and lung were removed from all the animals, weighed and processed for scintillation counting. Livers were made into a 30% homogenate in a known amount of water using a polytron tissue homogenizer. Aliquots (in triplicates) of 200 mL of the homogenate were transferred to scintillation vials for counting. All other organs were dissolved in 500 µL Solvable®. The vials were incubated at 50° C. overnight, then cooled prior to addition of 50 µL 200 mM EDTA, 25 µL 10 m HCl and 200 µL 30% H2O2. This mixture was incubated at room temperature for 1 h prior to addition of 5 mL scintillation cocktail and radioactivity in the samples measured by scintillation counting.

compounds were first screened for ability to inhibit thrombin binding to immobilized polyP, a high-throughput method for identifying polyP blockers (8). UHRA compounds 1-16, which vary in molecular weight and charge density, were individually screened in this assay (full data in TABLE 2). All the UHRA compounds inhibited polyP-thrombin interactions, but with efficacies that were influenced by charge density (i.e., the number of R groups), since the most potent inhibition required the presence of ≥5 such R groups per molecule (FIG. 1B). Eleven of the UHRA compounds had $IC_{50}$ values ≤10 nM for inhibiting thrombin binding to polyP, of which four were selected for further testing: UHRAs 8, 9, 10, and 14, which all inhibited thrombin binding to polyP with $IC_{50}$ values in the 5-8 nM range (TABLE 1). These four compounds vary in number from 7 to 24 positively charged R groups and vary in molecular weight from 10 to 23 kDa, allowing us to see if these two variables impact their antithrombotic effectiveness. Furthermore, these 4 compounds all have a ratio of molecular weight to number of polyP binding groups (kDa/R) value less than 1.5 (TABLE 2).

TABLE 1

In vitro inhibition of polyP activity by selected UHRA compounds

| Compound | Size (kDa) | R Groups | Thrombin Binding $IC_{50}$ nM | Thrombin Binding $IC_{50}$ ng/mL | Plasma Clotting Assay $EC_{double}$ polyP nM | Plasma Clotting Assay $EC_{double}$ polyP µg/mL | Plasma Clotting Assay $EC_{double}$ RNA µM | Plasma Clotting Assay $EC_{double}$ RNA µg/mL |
|---|---|---|---|---|---|---|---|---|
| UHRA 8 | 23 | 24 | 5.4 ± 1.8 | 124 ± 41 | 52 ± 15 | 1.20 ± 0.34 | 0.62 ± 0.21 | 14 ± 4.8 |
| UHRA 9 | 16 | 16 | 7.6 ± 2.0 | 122 ± 32 | 80 ± 16 | 1.28 ± 0.26 | 1.9 ± 0.59 | 30 ± 9.4 |
| UHRA 10 | 10 | 11 | 7.3 ± 3.7 | 73 ± 37 | 132 ± 38 | 1.32 ± 0.38 | 2.0 ± 0.58 | 20 ± 5.8 |
| UHRA 14 | 10 | 7 | 6.6 ± 2.4 | 66 ± 24 | 92 ± 13 | 0.92 ± 0.13 | 2.2 ± 0.65 | 22 ± 6.5 |

Results are: $IC_{50}$ for inhibiting thrombin binding to immobilized polyP (n = 5); and $EC_{double}$ (concentration needed to double the clotting time) in plasma clotting assays initiated with either 10 µM long-chain polyP ($EC_{double}$ polyP, n = 3) or 25 µg/mL polyguanylic acid ($EC_{double}$ RNA, n = 3). Data are reported in terms of both molarity and mass/volume ± SEM.

EXAMPLES

Example 1: Assays for PolyP Inhibitors

In order to have clinically useful polyP inhibitors we needed compounds with less inherent toxicity than the cationic polymers and proteins previously used in proof-of-principle studies of blocking polyP procoagulant activity (8, 9). Cationic polymers still seemed like the most likely candidates for highly potent polyP inhibitors, if we could separate polyP-inhibiting ability from the toxicity and protein/membrane binding properties of charged polymers like polyethylenimine and cationic PAMAM dendrimers. To address this problem, we tested a series of UHRA compounds (originally designed as non-toxic heparin reversal agents) for their ability to inhibit polyP activity in vitro and in vivo. The polymer scaffolds of this family of UHRA compounds were synthesized by anionic ring-opening polymerization of glycidol and α-methoxy-ω-epoxy polyethylene glycol (mPEG-400), which were then post-functionalized to introduce positively charged groups based on branched tertiary amines (FIG. 1A). The inclusion of a "shell" of short-chain PEG moieties in the UHRA compounds, together with the use of tertiary rather than primary amines, is designed to make these compounds much less toxic than previously-studied polyP inhibitors containing multiple primary amines.

Figure 7:
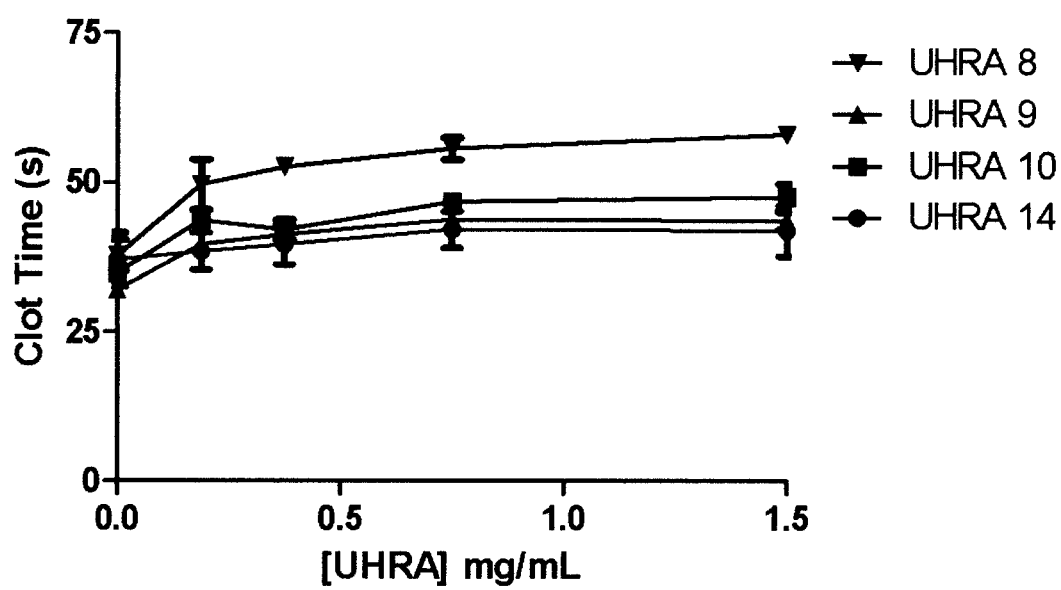
FIG. 7 shows doses of UHRA 8, 9, 10, and 14 up to 1.5 mg/mL having slight increases in tissue factor-initiated plasma clotting, wherein plasma clotting times were quantified at 37° C. using a STart4 coagulometer (Diagnostica Stago™) and all clotting assays used final concentrations of 33% pooled normal human plasma (George King Bio-Medical™), 25 μM liposomes (70:30 ratio of phosphatidylcholine to phosphatidylserine), 41.7 mM imidazole pH 7.0 and 8.33 mM $CaCl_2$, and a concentration of relipidated human tissue factor was chosen to give baseline clot times of approximately 35 seconds, with varying concentrations of each of the UHRA compound were mixed with pre-warmed tissue factor and plasma, followed by the addition of pre-warmed calcium chloride solution to induce clotting.

UHRA compounds inhibit polyP-thrombin binding and polyP-initiated plasma clotting in vitro. A panel of UHRA Because the thrombin binding assay is performed in the absence of plasma proteins that might compete for binding to polyP, we also examined the ability of the four selected compounds to inhibit thrombin binding in a modified aPTT clotting assay initiated by long-chain polyP (>1000 phosphates per chain) or polyguanylic acid (RNA). All four compounds doubled the polyP-initiated clotting times in the 50-150 nM range, and the RNA-initiated clotting times in the 1-2 µM range (TABLE 1). In contrast, even very high concentrations of UHRAs showed only minimal prolongation of the plasma clot time initiated by tissue factor (FIG. 7). This latter finding shows that UHRAs have minimal effect on the final common pathway of the plasma clotting system.

TABLE 2

16 UHRA Compounds Tested in vitro

| Compound | MW (kDa) | R Groups | kDa/R | Inhibition of Thrombin Binding to PolyP $IC_{50}$ (ng/mL) | Inhibition of Thrombin Binding to PolyP $IC_{50}$ (nM) |
|---|---|---|---|---|---|
| UHRA 1 | 116 | 33 | 3.52 | 1200 | 10.2 |
| UHRA 2 | 48 | 18 | 2.67 | 166 | 3.5 |
| UHRA 3 | 23 | 4 | 5.75 | 280000 | 12000 |
| UHRA 4 | 23 | 5 | 4.60 | 3100 | 136 |
| UHRA 5 | 23 | 11 | 2.09 | 50.1 | 2.18 |

TABLE 2-continued

16 UHRA Compounds Tested in vitro

| Compound | MW (kDa) | R Groups | kDa/R | Inhibition of Thrombin Binding to PolyP | |
|---|---|---|---|---|---|
| | | | | IC$_{50}$ (ng/mL) | IC$_{50}$ (nM) |
| UHRA 6 | 23 | 16 | 1.44 | 117 | 5.1 |
| UHRA 7 | 23 | 20 | 1.15 | 74 | 3.3 |
| UHRA 8 | 23 | 24 | 0.96 | 123 ± 18 | 5.4 ± 0.78 |
| UHRA 9 | 16 | 16 | 1.0 | 122 ± 14 | 7.6 ± 0.90 |
| UHRA 10 | 10 | 11 | 0.91 | 73 ± 17 | 7.3 ± 1.7 |
| UHRA 11 | 9 | 8 | 1.13 | 38 | 4.2 |
| UHRA 12 | 10 | 2 | 5.00 | 11000 | 1100 |
| UHRA 13 | 10 | 5 | 2.00 | 59 | 5.9 |
| UHRA 14 | 10 | 7 | 1.42 | 66 ± 11 | 6.6 ± 1.1 |
| UHRA 15 | 5 | 2 | 2.50 | 124 | 25 |
| UHRA 16 | 5 | 1 | 5.00 | 18000 | 3500 |

UHRA compounds were screened for ability to inhibit thrombin binding to immobilized polyP as described in Methods.
"R-groups" refers to the number of binding groups per polymer (see FIG. 1A for a general overview of UHRA structure).
IC$_{50}$ values (given in concentrations by weight and molarity) indicate the concentration of UHRA needed to yield 50% inhibition of thrombin binding to polyP (n = 1-5, data reported as mean ± SEM for n > 3 and mean for n < 3).
UHRA compounds 8, 9, 10, and 14 (shaded) were chosen for further study.

Example 2: Thermodynamic Parameters for Interaction of UHRA with PolyP

Both the thrombin/polyP binding assays and clotting assays were performed at ionic strengths lower than that of plasma. Therefore, isothermal titration calorimetry was used to determine the parameters for binding of polyP to UHRA 8, 9, 10 and 14 at physiologic ionic strength (FIG. 8), in order to better predict the concentrations of these UHRA compounds that might be needed to inhibit polyP function in blood. UHRA 8, 9, 10 and 14 bound to polyP with K$_d$ values in the 0.7 to 2.2 µM range (TABLE 3).

TABLE 3

Thermodynamic Parameters for Interaction of UHRA with PolyP$_{75}$ Determined by Isothermal Titration Calorimetry

| Compound | N$^a$ | K$_d$ (µM)$^a$ | ΔG (kcal/mol)$^b$ | ΔH (kcal/mol)$^a$ | TΔS (kcal/mol)$^b$ |
|---|---|---|---|---|---|
| UHRA 8 | 1.23 | 0.727 ± 0.01 | −8.34 ± 0.01 | −107 ± 0.3 | −98.7 ± 0.3 |
| UHRA 9 | 2.66 ± 0.007 | 1.71 ± 0.04 | −7.83 ± 0.01 | −59.5 ± 0.3 | −51.7 ± 0.3 |
| UHRA 10 | 2.98 ± 0.007 | 1.83 | −7.79 | −48.9 ± 0.2 | −41.1 ± 0.2 |
| UHRA 14 | 3.22 ± 0.01 | 2.24 ± 0.05 | −7.67 ± 0.01 | −36.6 ± 0.3 | −28.9 ± 0.3 |

$^a$Obtained from isothermal titration calorimetry experiments
$^b$Calculated from the equation ΔG = ΔH − TΔS = −RTlnK$_a$ All data were collected in PBS at pH 7.4 and 25° C. Values given represent an average from two independent titrations and standard deviations are indicated in parentheses. N: number of moles of UHRA binding per mole of polyP$_{75}$; K$_d$: dissociation constant; ΔG: free energy change; ΔH: enthalpy change; TΔS: entropy change. UHRAs exhibited binding affinities in the micromolar range (0.7-2.2 µM) to polyP$_{75}$ (a polyP preparation with median polymer lengths of approximately 75 phosphate units). UHRA-8 (23 kDa with 24 binding groups) exhibited the highest binding affinity (K$_d$=0.727 µM) among the inhibitors. At the similar inhibitor molecular weight, the greater the number of binding groups per UHRA molecule, the stronger the affinity to polyP (UHRA 10 vs UHRA 14). There was no significant difference in free energy of binding (ΔG) among the polymers; however, the enthalpy of binding (ΔH) increased with an increase in molecular weight as well as the number of binding groups on UHRAs.

Figure 2:
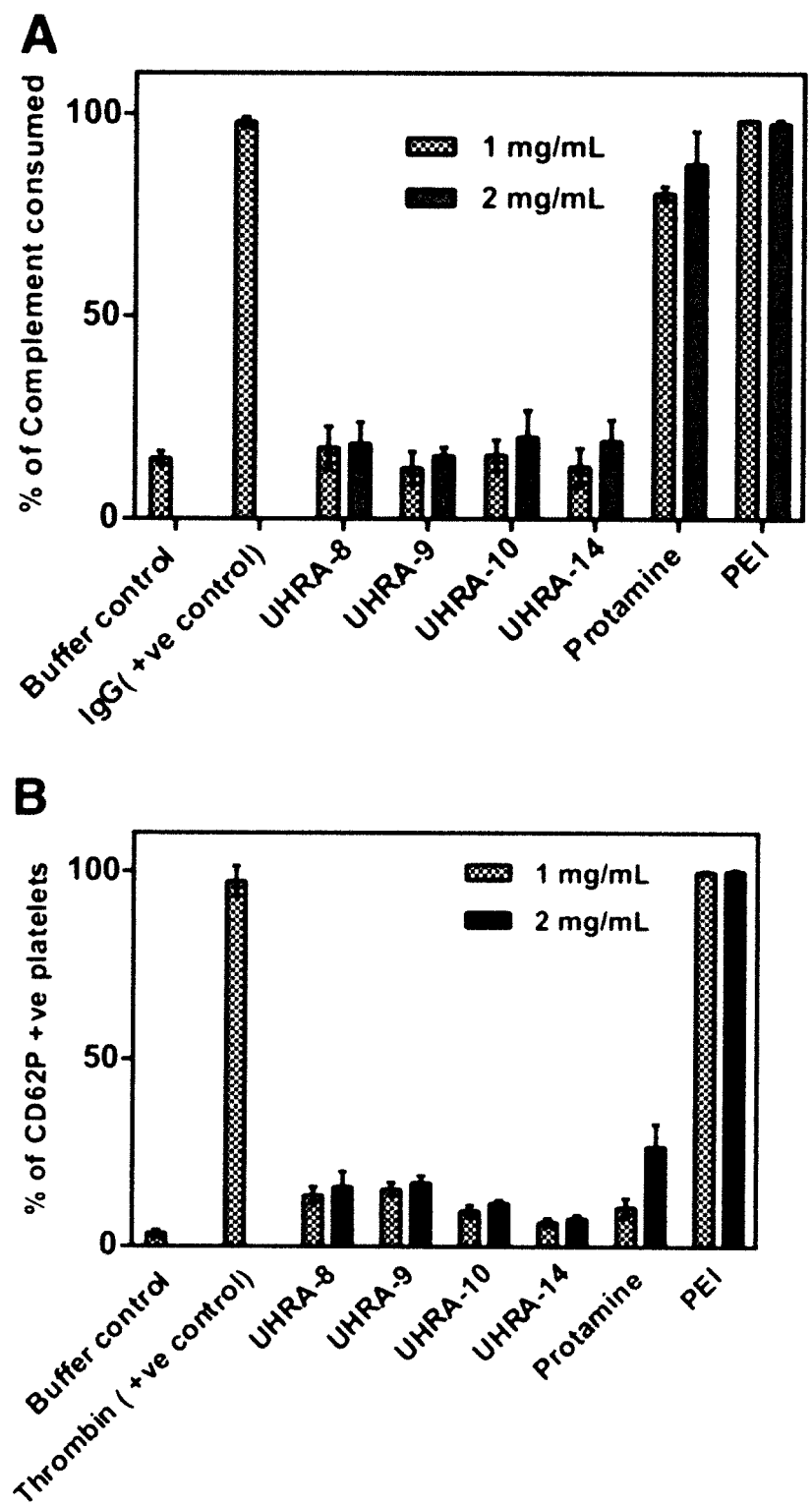
FIG. 2 shows biocompatibility of UHRAs compared to other polyP inhibitors: (A) graphs the ability of UHRA compounds, protamine sulfate (PS) and PEI (tested at 1 or 2 mg/mL) to activate complement in human serum as a measurement of sheep erythrocyte complement consumption, wherein the heat-aggregated human IgG (1 mg/mL) and PBS were the positive and negative controls, respectively. The UHRAs did not activate complement compared to buffer controls, while protamine and PEI showed high levels of complement activation in the assay; and (B) graphs the ability of UHRA compounds, protamine and PEI (tested at 1 and 2 mg/mL) to activate platelets in human platelet-rich plasma (PRP) as measured by flow cytometry for expression of platelet activation marker CD62P, where bovine thrombin (at 1 IU/mL) was used as the positive control, and PBS alone was the negative control ("buffer control"). The UHRAs showed low levels of platelet activation compared to PEI.

Example 3: Biocompatibility of UHRA Compounds Compared to Previously Identified PolyP Inhibitors To examine whether the unique structure of the UHRA compounds allowed them to inhibit polyP with reduced toxic side effects, we investigated the interaction of UHRAs with blood components in comparison to other, previously reported polyP inhibitors such as polyethylenimine (PEI) and protamine sulfate (8). Complement assays were performed in human serum at 37° C. by measuring the total complement consumption using antibody-sensitized sheep erythrocyte assay. Compared to buffer controls, complement activation was undetectable with UHRAs even at 2 mg/mL (FIG. 2A). PEI and protamine, on the other hand, strongly activated complement. Platelet activation was studied by measuring CD62P expression in platelet-rich plasma. UHRAs exhibited lower levels of platelet activation (10-15%), compared to protamine and PEI, which activated platelets by about 30% and 100% respectively, when tested at the highest dose (FIG. 2B).

Figure 9:
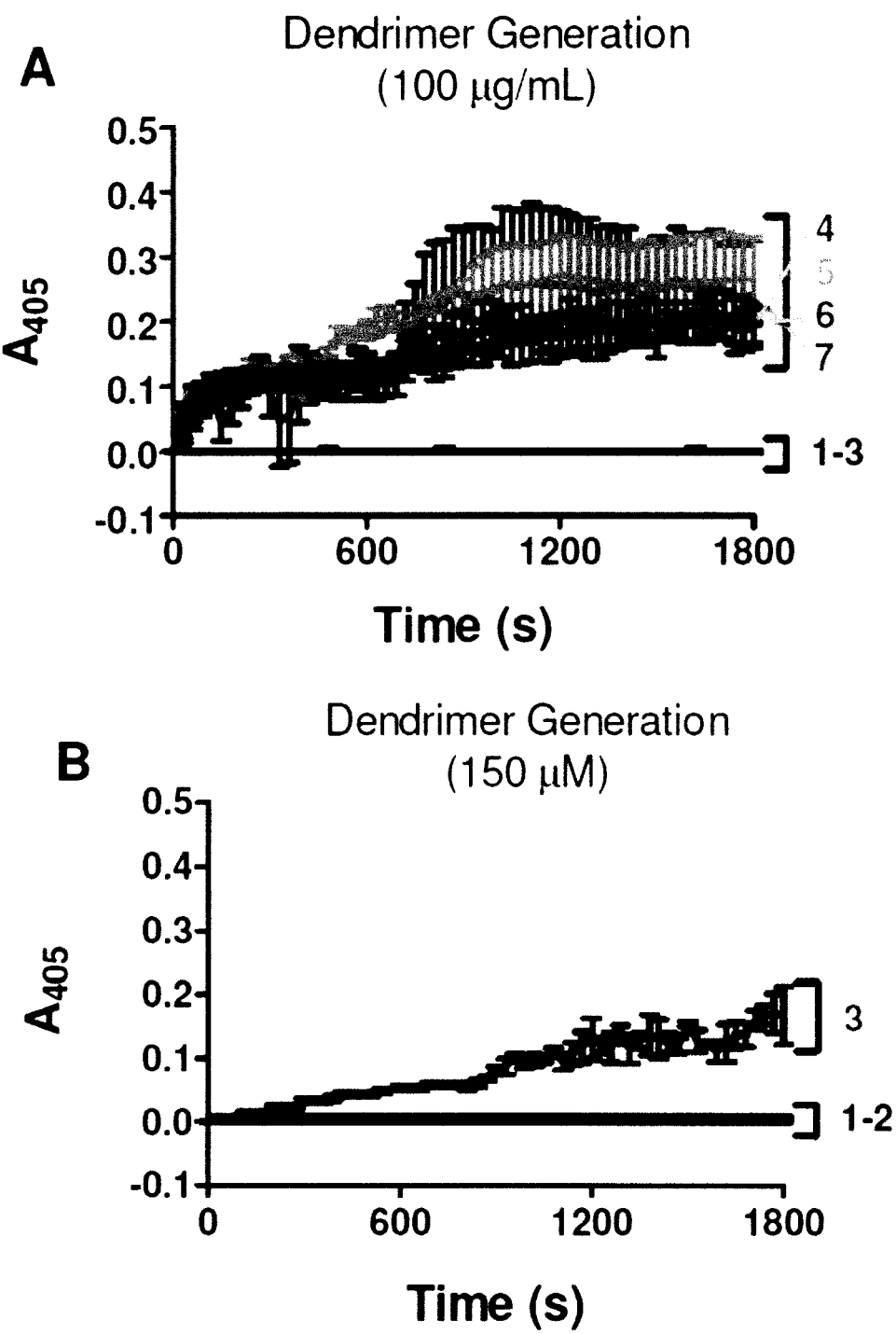
FIG. 9 shows PAMAM dendrimers, but not UHRA compounds induce fibrinogen aggregation, wherein turbidity assays were adapted from previous reports of dendrimer-induced fibrinogen aggregation (30), and the PAMAM dendrimer generations 1-7, or UHRA compounds 8, 9, 10 or 14, were diluted in TBSC (50 mM Tris-HCl pH 7.4, 100 mM NaCl, 2.5 mM $CaCl_2$, 0.02% $NaN_3$) and added to wells of a 96-well plate, where an equal volume of 4 mg/mL human fibrinogen (Enzyme Research Laboratories™) diluted in TBSC was added (final fibrinogen concentration of 2 mg/mL) immediately before recording the absorbance at 405 nm every 30 seconds for 30 minutes. The graphs shown are baseline-subtracted mean±SEM, n=3 for all experiments. (A) At concentrations of 100 μg/mL, PAMAM dendrimer generations 4-7 all showed increased turbidity, indicating the induction of fibrinogen aggregates; (B) while PAMAM dendrimer generations 1-3 did not show signs of fibrinogen aggregation at 100 μg/mL, when tested at 150 μM (or 0.21, 0.49, and 1.0 mg/mL respectively), generation 3 PAMAM dendrimer also caused detectable turbidity, indicative of inducing fibrinogen aggregation; and (C) UHRA compounds showed no detectable fibrinogen aggregation even at concentrations up to 1.5 mg/mL. (Note that 1.5 mg/mL UHRA 8 is 150 μM.).
Figure 9:
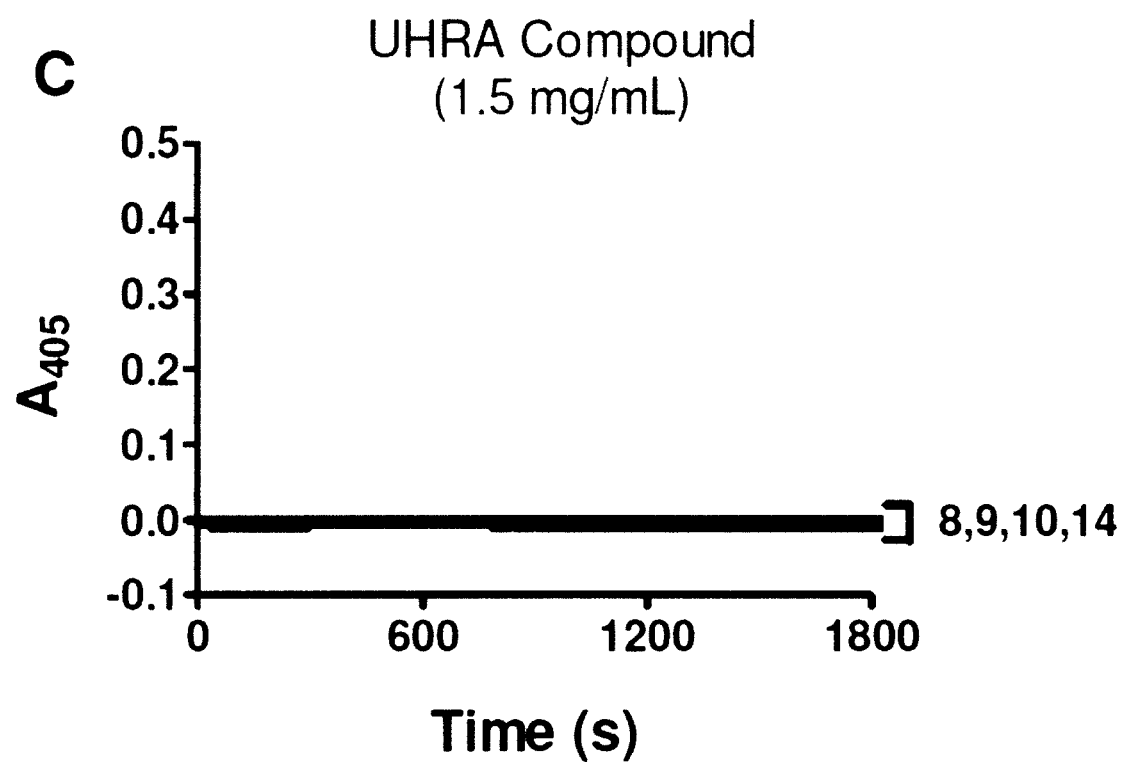

Cationic PAMAM dendrimers have been identified as proof-of-principle polyP blockers (8, 9), although this type of dendrimer is reported to have significant toxicity in vitro and in vivo including the ability to induce fibrin(ogen) aggregation and induce a state similar to disseminated intravascular coagulation (DIC) (10-13). Furthermore, the in vivo toxicity of amine-terminated PAMAM dendrimers increases with generation (reviewed by (13)), which is unfortunate because their effectiveness in blocking polyP also increases with generation (8, 9). The ability of UHRAs 8, 9, 10 and 14 versus cationic PAMAM dendrimers (generations 1-7) were examined for their ability to induce fibrinogen aggregation (FIG. 9). Even when tested at 1.5 mg/mL, none of the UHRA compounds showed evidence of inducing fibrinogen aggregation. On the other hand, generation 3 to 7 PAMAM dendrimers caused fibrinogen aggregation at doses from 0.2 to 1 mg/mL, confirming and expanding a previous report of generation 7 PAMAM dendrimers inducing fibrinogen aggregation and a DIC-like state (11).

Figure 10:
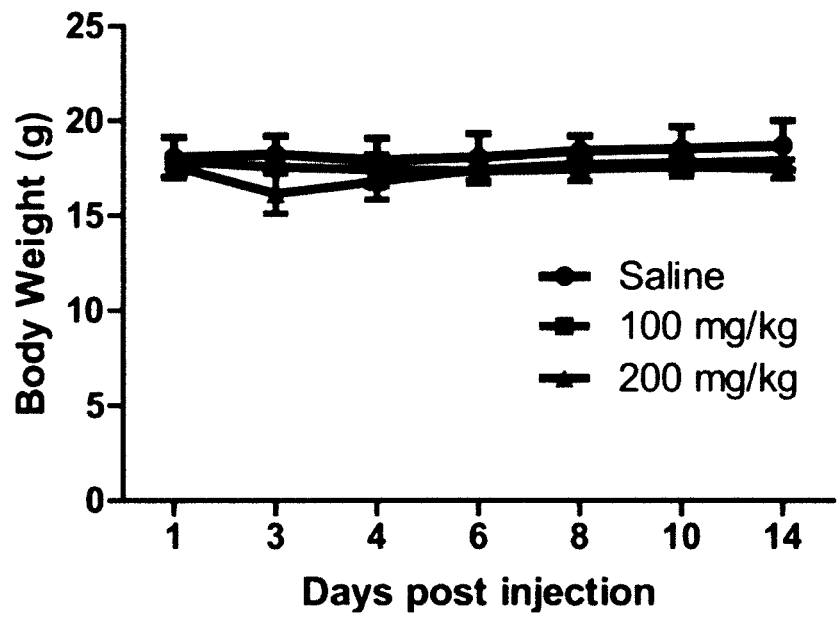
FIG. 10 shows non-toxicity of UHRA 10 in vivo, wherein dose tolerance of UHRA was examined in mice by the administration of 100 mg/kg, 200 mg/kg of UHRA-10 or saline control to female Balb/C mice, wherein graph (A) shows no change in the body weights (n=3, reported as mean±S.D.) of mice injected with either saline (black circles) or UHRA 10 at doses of 100 (red squares) or 200 mg/kg (blue triangles); and (B) shows that serum lactate dehydrogenase (LDH) levels in mice injected with saline or with 100 or 200 mg/kg UHRA 10 were all within the normal ranges for serum LDH in mice.
Figure 10:
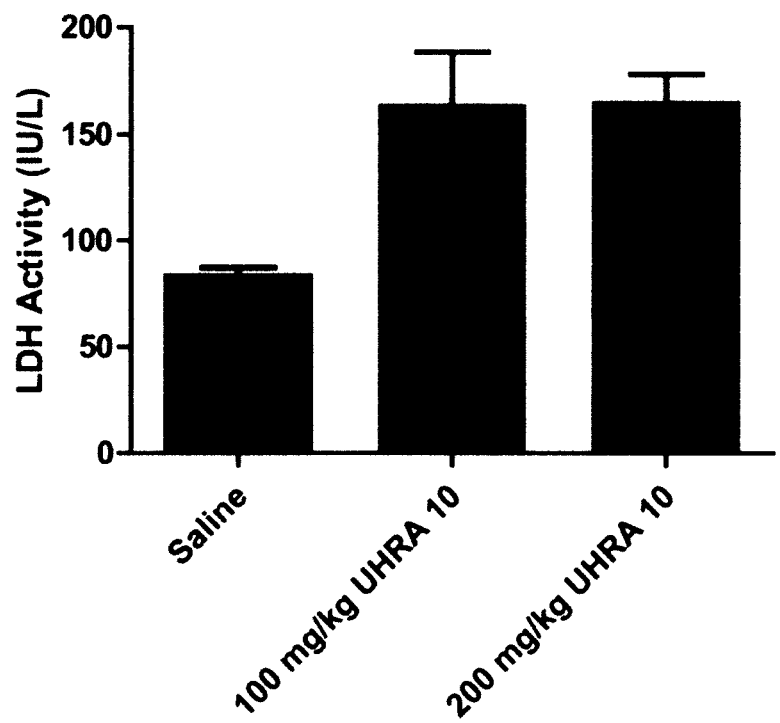

As shown in FIG. 10A, there was no change in the body weights (n=$_3$, reported as mean±S.D.) of mice injected with either saline (black circles) or UHRA 10 at doses of 100 (red squares) or 200 mg/kg (blue triangles). Similarly, FIG. 10B shows serum lactate dehydrogenase (LDH) levels in mice injected with saline or with 100 or 200 mg/kg UHRA 10 were all within the normal ranges for serum LDH in mice, which are typically below 400 U/mL. (31, 32). There was also no evidence of abnormalities in the histopathological analysis, further confirming the non-toxic nature of UHRA 10 in vivo (data not shown).

Figure 3:
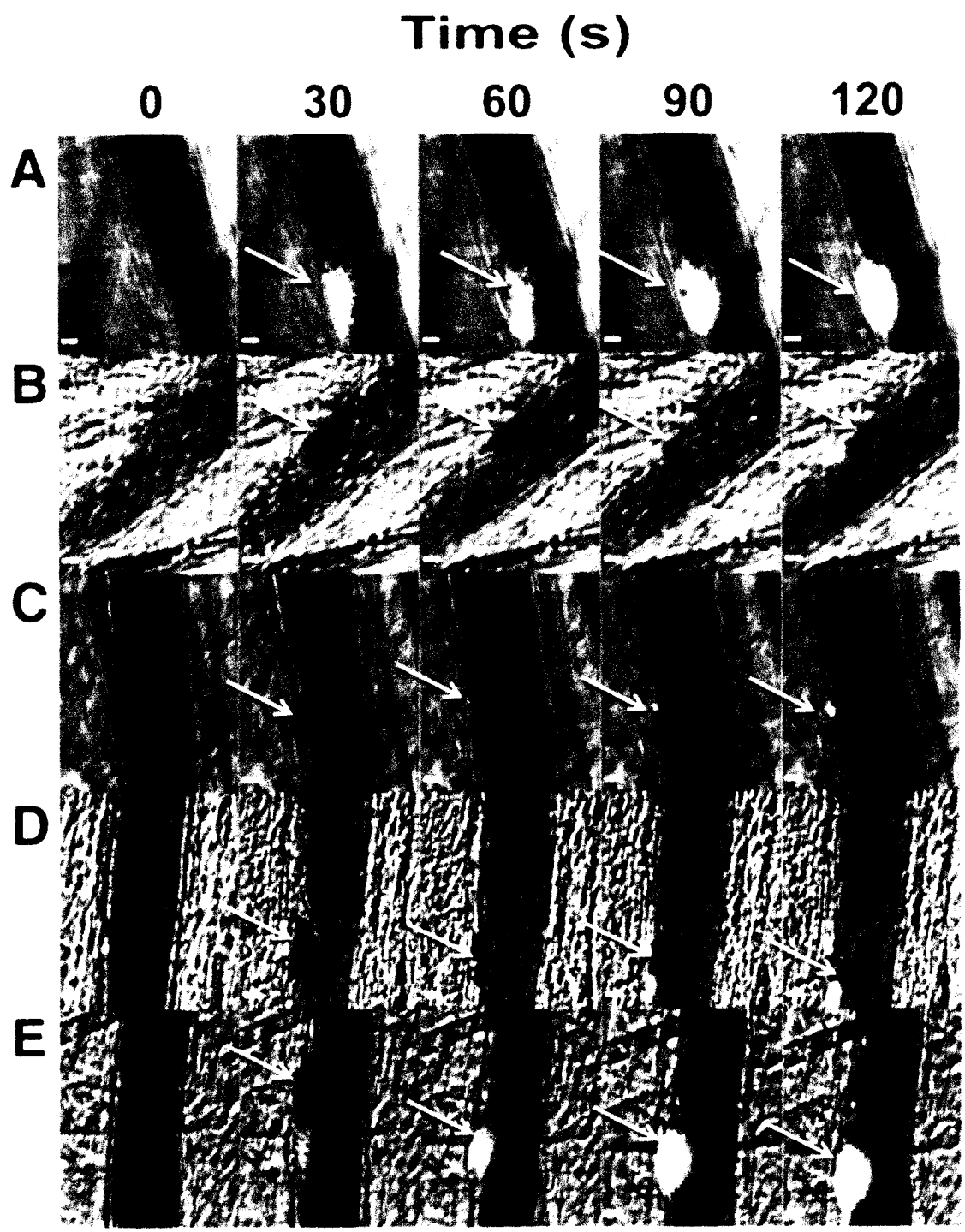
FIG. 3 shows UHRA compounds inhibit thrombus formation in mouse cremaster arterioles, with (A-E) showing binarized images from one representative injury each showing the accumulation of platelets and fibrin (arrows) at various time intervals up to 120 seconds after laser-induced injury to the vessel wall in mice administered either (A) saline or the following UHRA compounds at 40 μg/g: (B) UHRA 8, (C) UHRA 9, (D) UHRA 10, or (E) UHRA 14 (Scale bars: 10 μm) and (F-I) show the statistical analyses of the effect of administering UHRA compound on thrombus formation. The data was collected from 27-30 injuries to 5 mice for each group, with the median integrated fluorescence intensities (non-binarized) plotted versus time for accumulation of (F) for platelets and (H) for fibrin, and the area under the curve (total fluorescence intensity) was plotted for accumulation of (G) in platelets and (I) in fibrin (each point representing one injury), and the median values were evaluated by Mann-Whitney test, both UHRA 9 and 10 significantly reduced total accumulation of platelets and fibrin compared to control. *P<0.05, ***P<0.0005.
Figure 3:
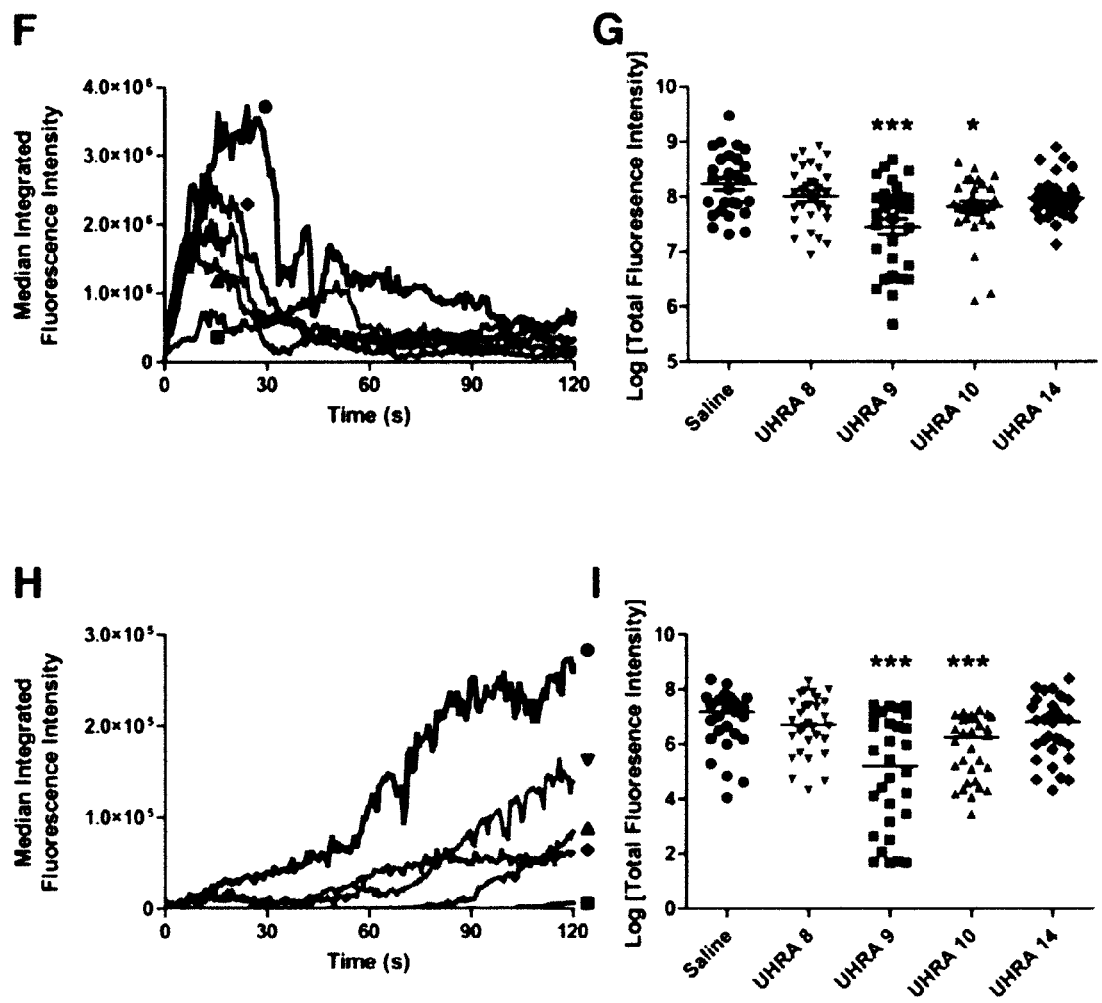
Figure 4:
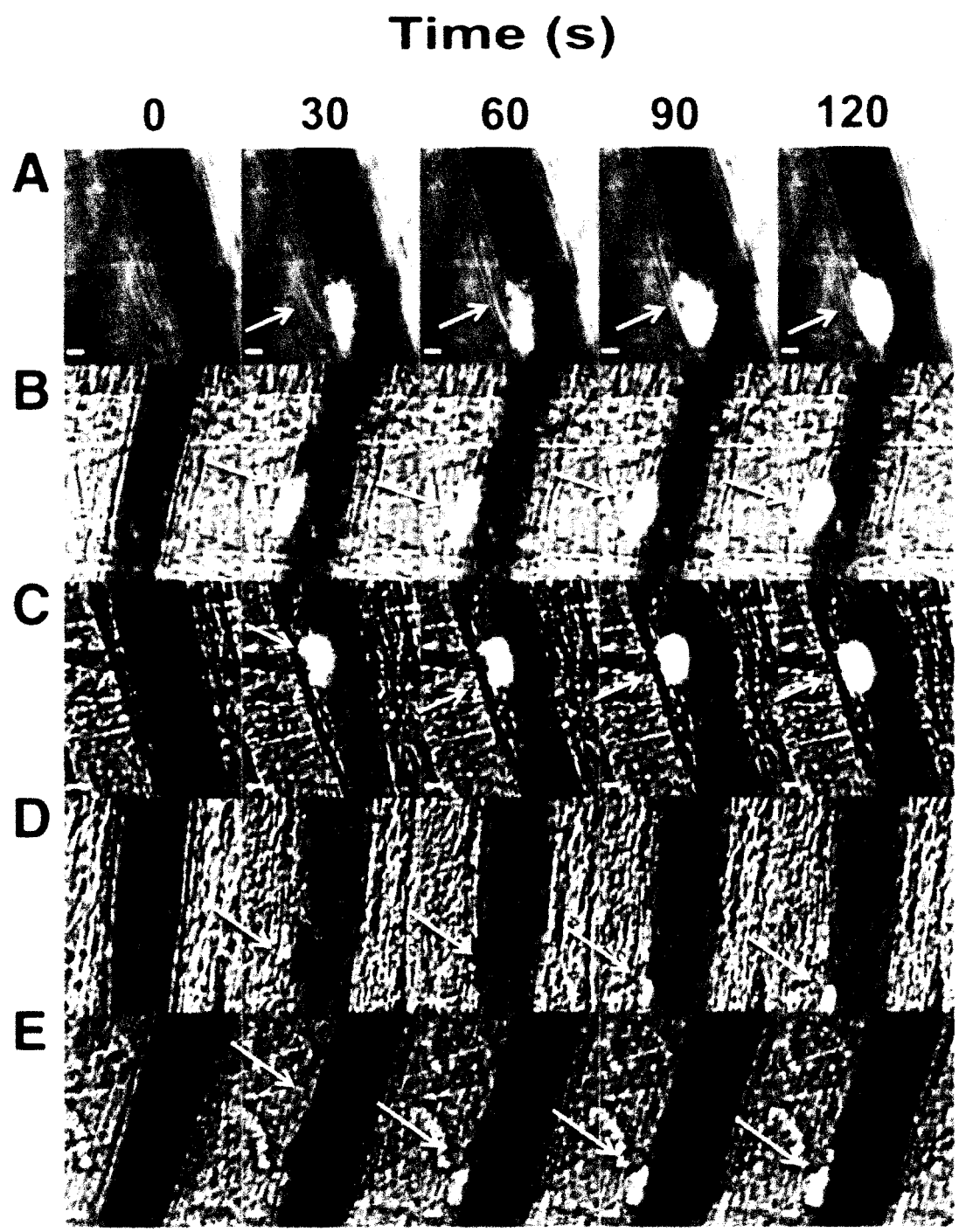
FIG. 4 shows UHRA 10 inhibits thrombus formation in mouse cremaster arterioles in a dose-dependent manner in (A-E) which shows binarized images from one representative injury each showing the effects on accumulation of platelets and fibrin (arrows) at various time intervals up to 120 seconds after laser-induced injury to the vessel wall in mice administered either (A) saline or UHRA 10 at (B) 10 μg/g, (C) 20 μg/g, (D) 40 μg/g, or (E) 80 μg/g (Scale bars: 10 μm) and (F-I) show the statistical analyses of the dose-dependent attenuation of thrombus formation by UHRA 10; data were collected from 27-30 injuries to 5 mice for each group, with the median integrated fluorescence intensities (non-binarized) plotted versus time for accumulation of (F) platelets and (H) fibrin and the area under the curve (total fluorescent intensity) for each individual injury was plotted for accumulation of (G) platelets and (I) fibrin (each point represents one injury). (Note: data for saline control and UHRA at 40 μg/g are in common with the data from FIG. 3 and are therefore repeated here in panels A and D, and the blue lines and data points in panels F-I.) with median values being compared to saline control for statistical significance by Mann-Whitney test, where UHRA 10 significantly reduced platelet accumulation at doses of 20 and 40 μg/g, and significantly reduced fibrin accumulation at doses of 40 and 80 μg/g. *P<0.05, P<0.005, *P<0.0005.
Figure 4:
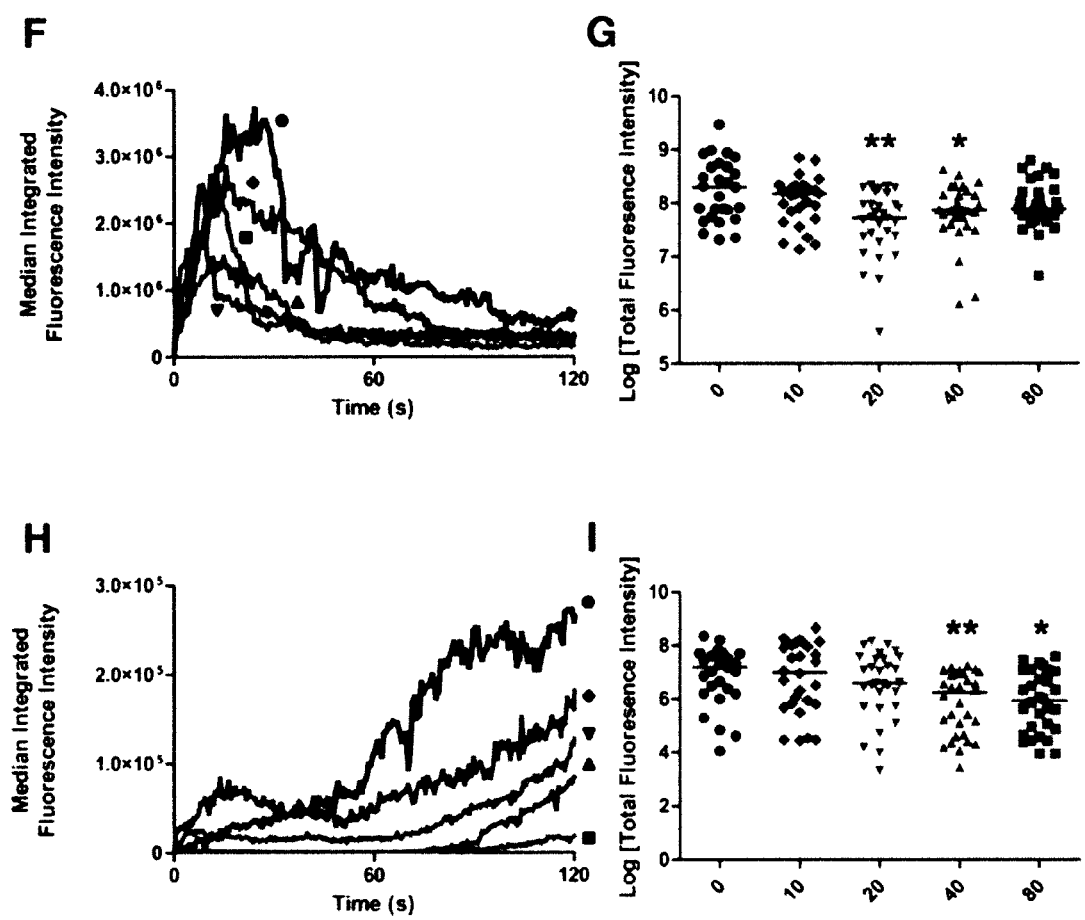

Example 4: UHRA Compounds are Antithrombotic in Two Mouse Models of Arterial Thrombosis To test the antithrombotic effectiveness of UHRA compounds in vivo, two mouse models of pathological thrombus formation were employed: laser-induced injury to cremaster arterioles and $FeCl_3$-induced injury to carotid arteries. Initially, UHRAs 8, 9, 10, or 14 were administered intravenously at 40 μg/g to mice after which cremaster arterioles were injured (FIG. 3). UHRAs 9 and 10 significantly reduced the accumulation of both platelets and fibrin, with UHRA 9 resulting in a 73% decrease in median total platelet fluorescent intensity (P=0.0006) and a 99% decrease in median fibrin total fluorescent intensity (P=0.0001) compared to saline control. UHRA 10 was similarly effective, resulting in a 63% reduction in total platelet fluorescent intensity (P=0.018) and an 88% reduction in fluorescent fibrin accumulation (P=0.0009). While UHRAs 8 and 14 reduced median platelet total fluorescent intensity by 41 and 60% and median fibrin total fluorescent intensity by 66 and 56% respectively, these decreases were not statistically significant from saline controls (FIG. 3). We then varied the dose of UHRA 10 to establish its range of effectiveness (FIG. 4). UHRA 10 significantly reduced median total platelet fluorescence at doses of 20 and 40 μg/g (P=0.001 and P=0.018 respectively) with a maximum inhibition of 73% at the 20 μg/g dose. Median total fibrin fluorescence was significantly inhibited at doses of 40 and 80 μg/g (P=0.0009 and P=0.0013 respectively), with a maximum inhibition of 94% at the 80 μg/g dose.

Figure 5:
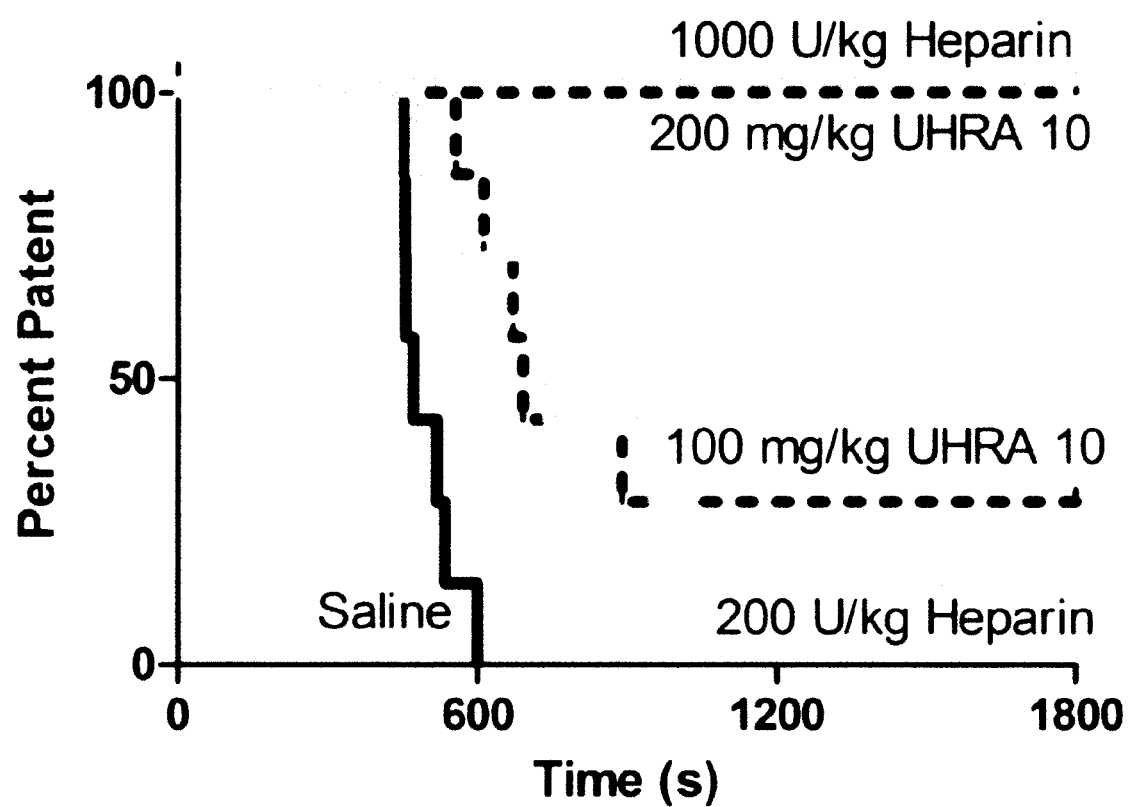
FIG. 5 shows UHRA 10 delays time to occlusion in a mouse carotid artery model of thrombosis, where artery patency was monitored by Doppler flow probe following induction of $FeCl_3$-mediated injury, and plotted versus time, where the saline control (solid black), unfractionated heparin (grey 1000 and 200 U/kg) and for UHRA 10 (dashed black 100 and 200 mg/kg), where both heparin and UHRA 10 significantly delayed median time to occlusion in a dose-dependent manner (P<0.0001) and Heparin at 200 U/kg was not significantly more effective than UHRA 10 at 100 μg/g at maintaining artery patency (P=0.85), while both treatment conditions significantly increased median patency time versus saline control (P=0.0004 for UHRA 10 and P=0.007 for heparin), the UHRA 10 at 200 μg/g or heparin at 1000 U/kg resulted in 100% patency over the 30 minute period for all mice (n=7 for all conditions)—statistical significance was assessed by log-rank analysis.

The ability of UHRA 10 to inhibit mouse carotid arterial thrombosis induced by topical application of $FeCl_3$ was also examined (FIG. 5), and it was found that a dose of 100 μg/g UHRA 10 performed as well as a dose of 200 U/kg heparin, as both treatments significantly increased the median patency time (P=0.0004 for UHRA 10 and P=0.007 for heparin). A dose of 200 μg/g UHRA 10 was as effective as 1000 U/kg heparin in completely blocking detectable thrombus formation for 30 minutes.

Figure 6:
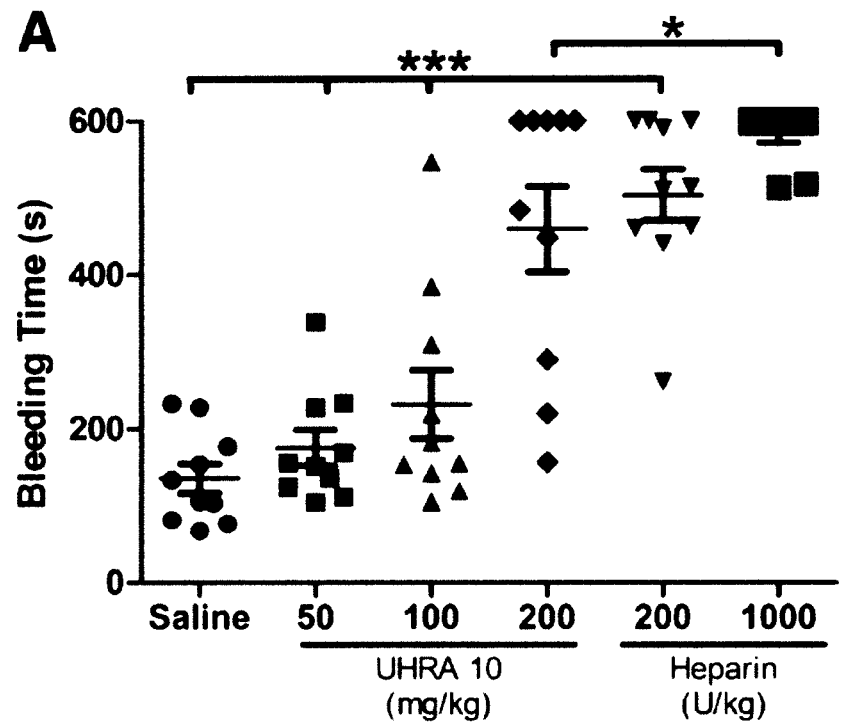
FIG. 6 shows antithrombotic doses of UHRA 10 caused less bleeding than did heparin in a mouse tail bleeding model: with (A) showing bleeding times in mice treated with 200 U/kg unfractionated heparin having significantly longer tail bleeding times than did either saline control mice or mice treated with 50 or 100 μg/g UHRA 10 and similarly, mice treated with 1000 U/kg heparin had significantly longer bleeding times than did mice treated with 200 μg/g UHRA 10; and (B) showing blood loss (quantified as mg hemoglobin collected during 30 min) in mice treated with either 200 or 1000 U/kg heparin had significantly higher hemoglobin loss than did mice treated with saline and mice treated with 1000 U/kg heparin had significantly more hemoglobin loss than did mice treated with 50 or 100 μg/g UHRA 10, while mice treated with 1000 U/kg heparin had no significant difference in hemoglobin loss compared to mice treated with 200 μg/g UHRA 10—Statistical significance was assessed by individual Student's t-tests; *P<0.05, P<0.005, *P<0.0005.
Figure 6:
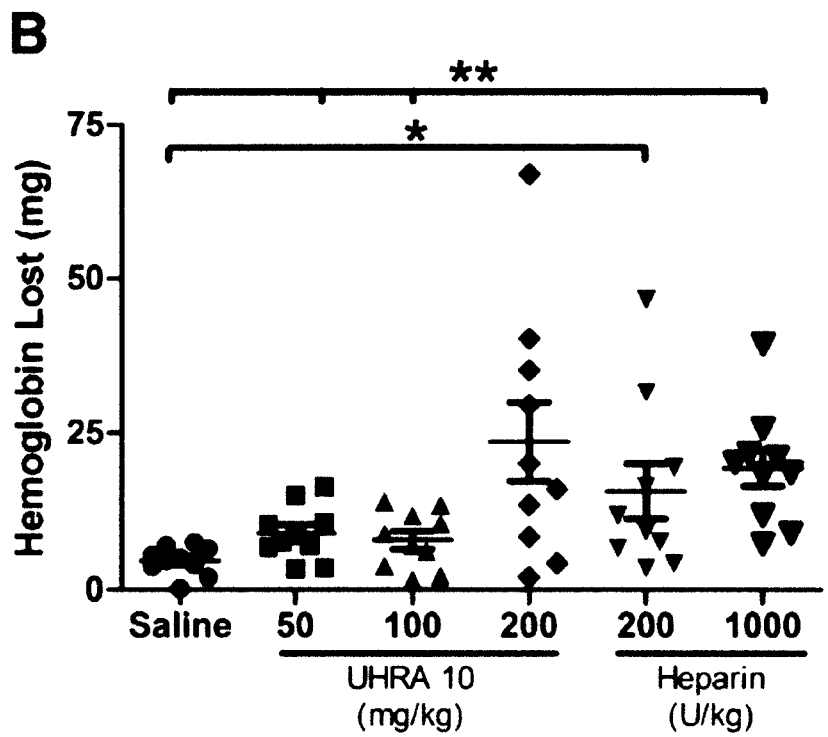
Figure 8:
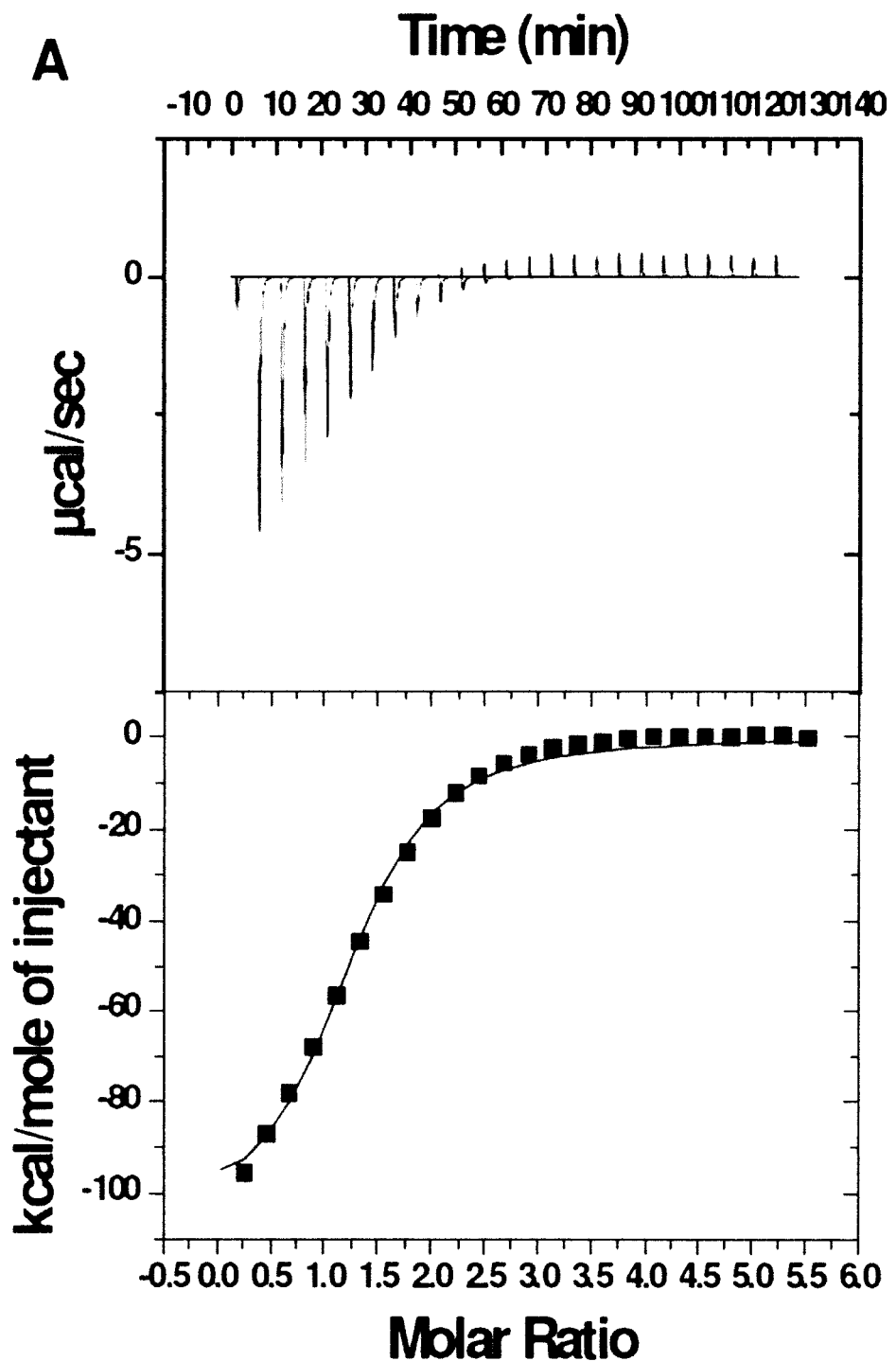
FIG. 8 shows isothermal titration calorimetry analysis for UHRA-polyP binding. (A-D) Raw data and integral heats for the titration of different UHRAs (A UHRA-8; B UHRA-9; C UHRA-10; D UHRA-14) into $polyP_{75}$ in 10 mM phosphate buffered saline (PBS) at pH 7.4 and 25° C., wherein a one-site binding model was used to obtain fit for all the titration data. Thermodynamic parameter analysis is presented in TABLE 3.
Figure 8:
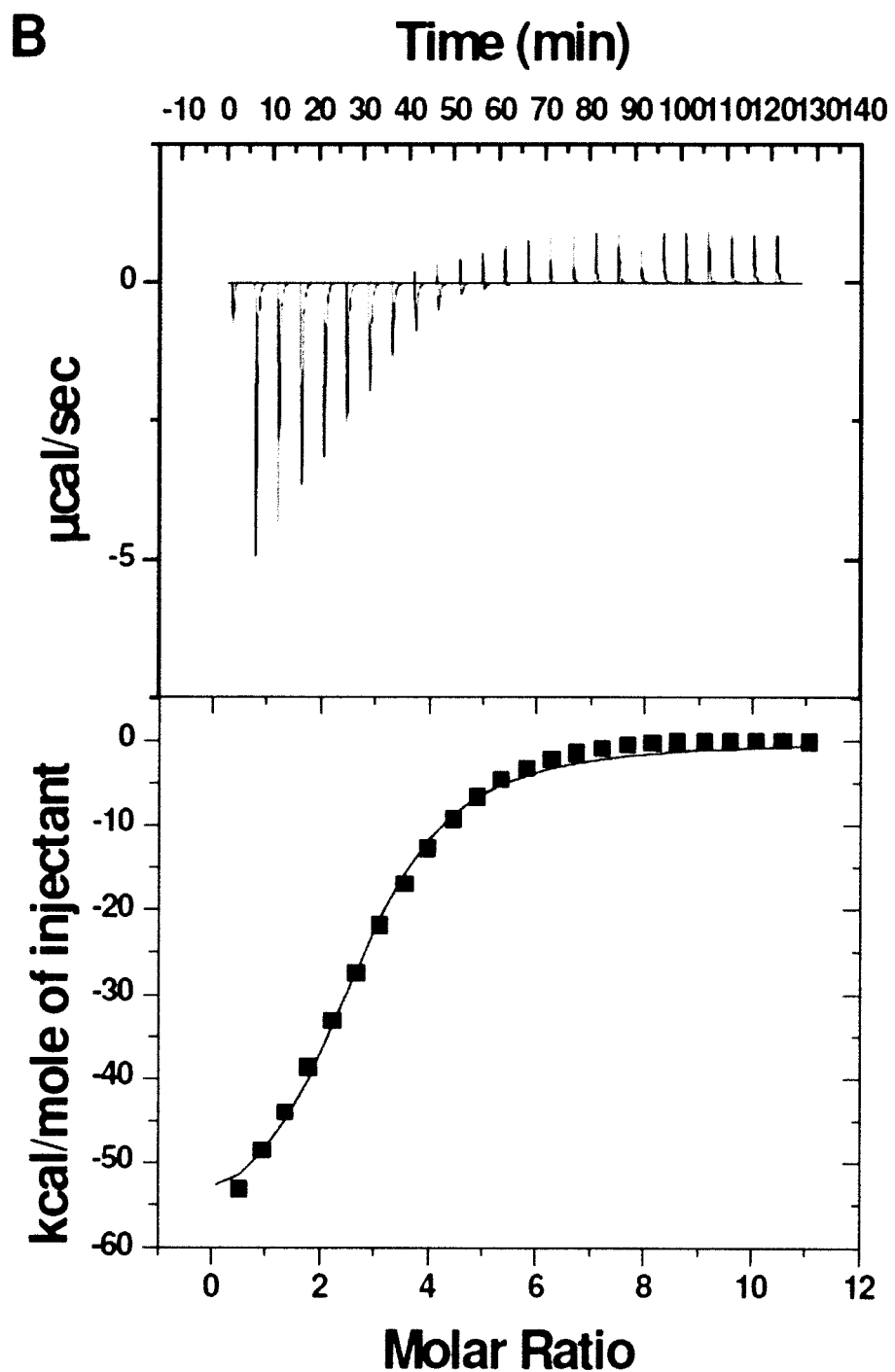
Figure 8:
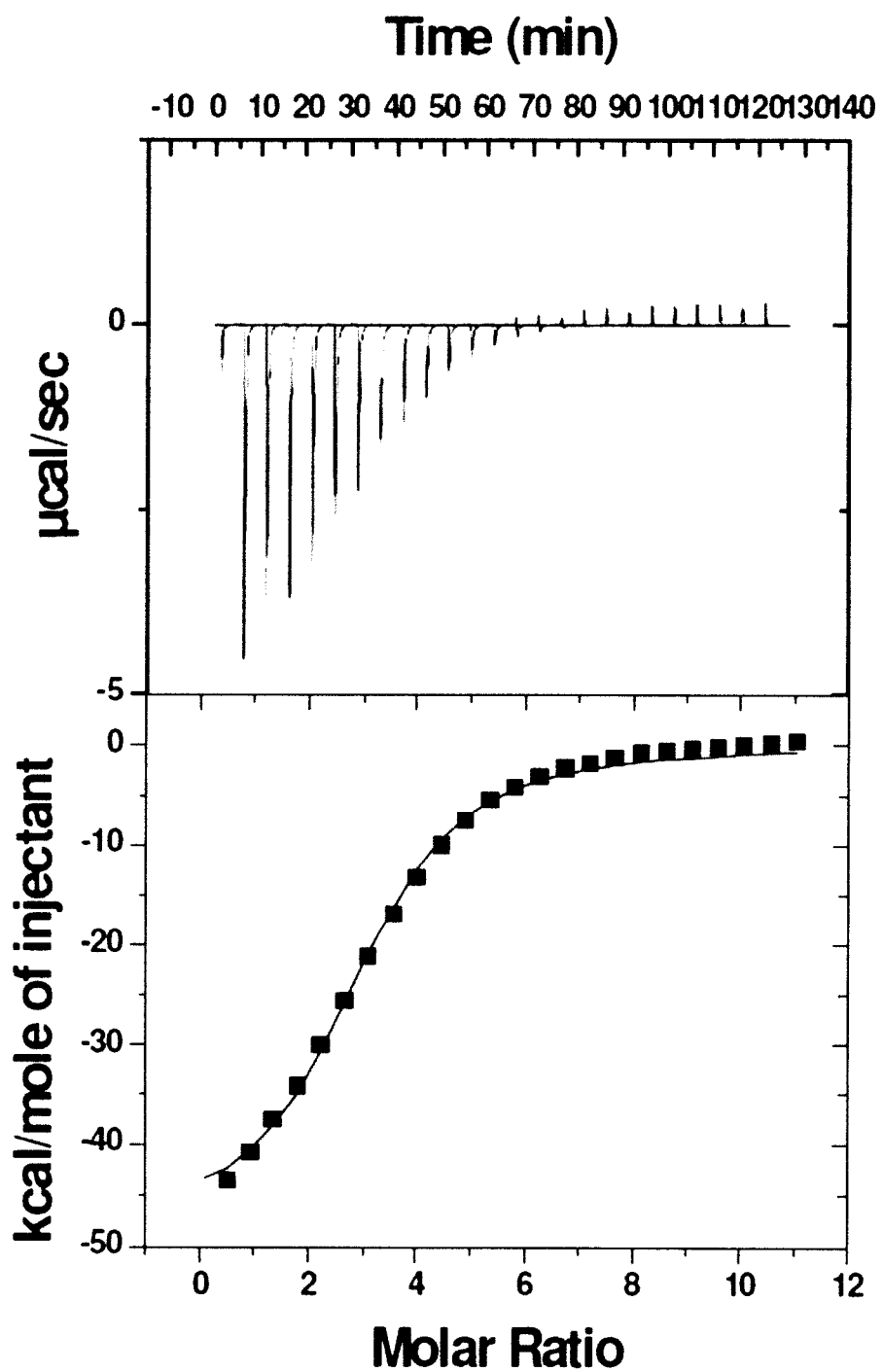
Figure 8:
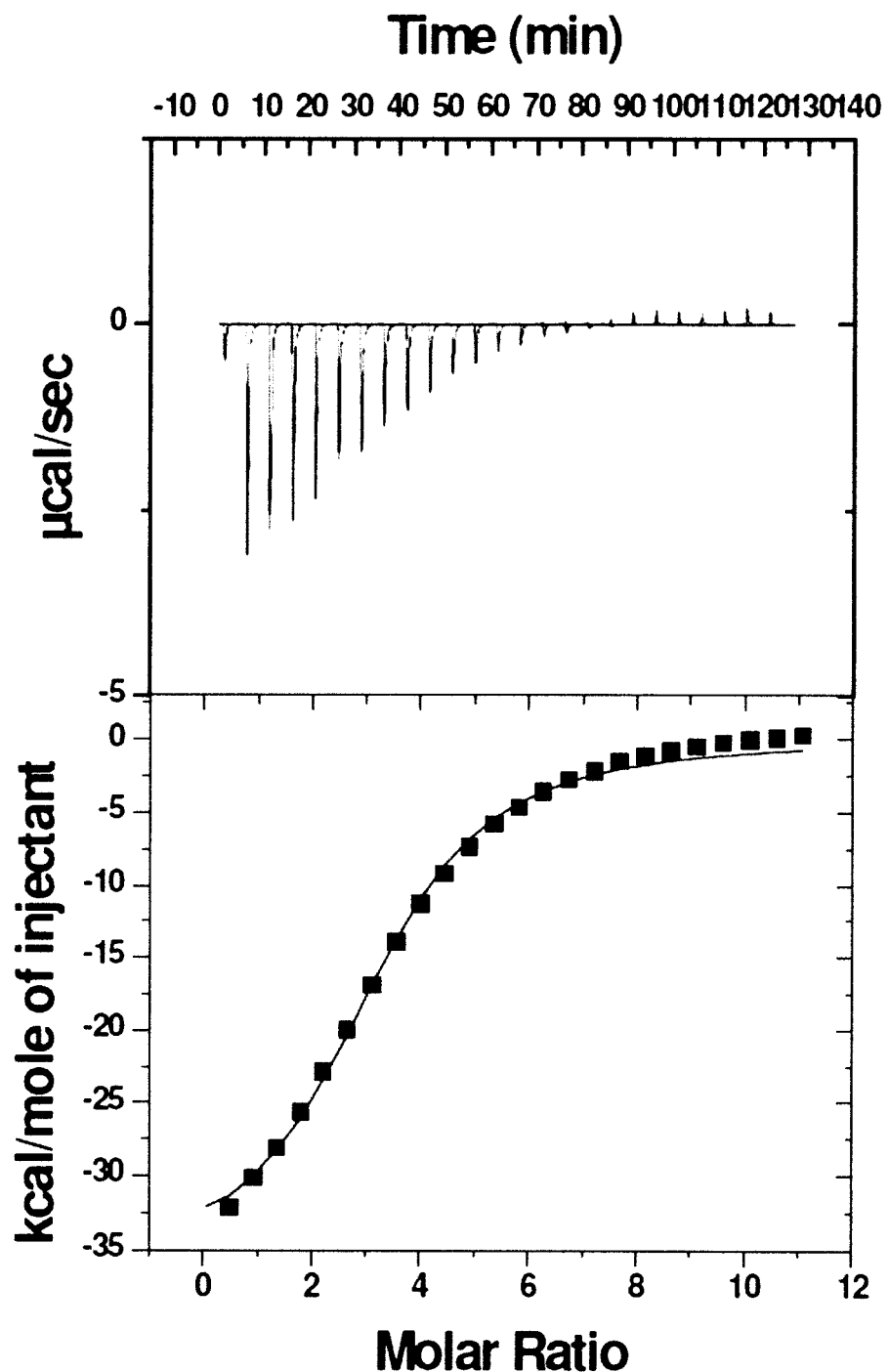

Example 5: Antithrombotic Doses of UHRA 10 Cause Less Bleeding Compared to Heparin In order to test if UHRA 10 causes less bleeding than heparin, a mouse tail bleeding model was used to compare treatment with 50, 100, and 200 μg/g doses of UHRA 10 to treatment either with saline alone or with 200 or 1000 U/kg doses of heparin (FIG. 6). Mice treated with a 200 U/kg dose of heparin all had significantly longer bleeding times compared to saline controls or mice treated with 50 or 100 μg/g doses of UHRA 10 (P<0.0001, FIG. 6A). As expected, heparin-treated mice also lost significantly more hemoglobin due to bleeding than did saline-treated mice (P=0.022, FIG. 6B), and although mice treated with 50 or 100 μg/g UHRA 10 lost less hemoglobin (10.8±2.4 and 7.9±1.4 mg respectively) than heparin treated mice (15.7±4.4 mg), the differences were not statistically significant (P=0.16 and P=0.11 respectively). Mice treated with the highest dose of UHRA 10 (200 μg/g) had significantly shorter bleeding times (P=0.047), but no significant difference in hemoglobin lost (P=0.55) compared to mice treated with 200 U/kg heparin (FIG. 8).

Figure 11:
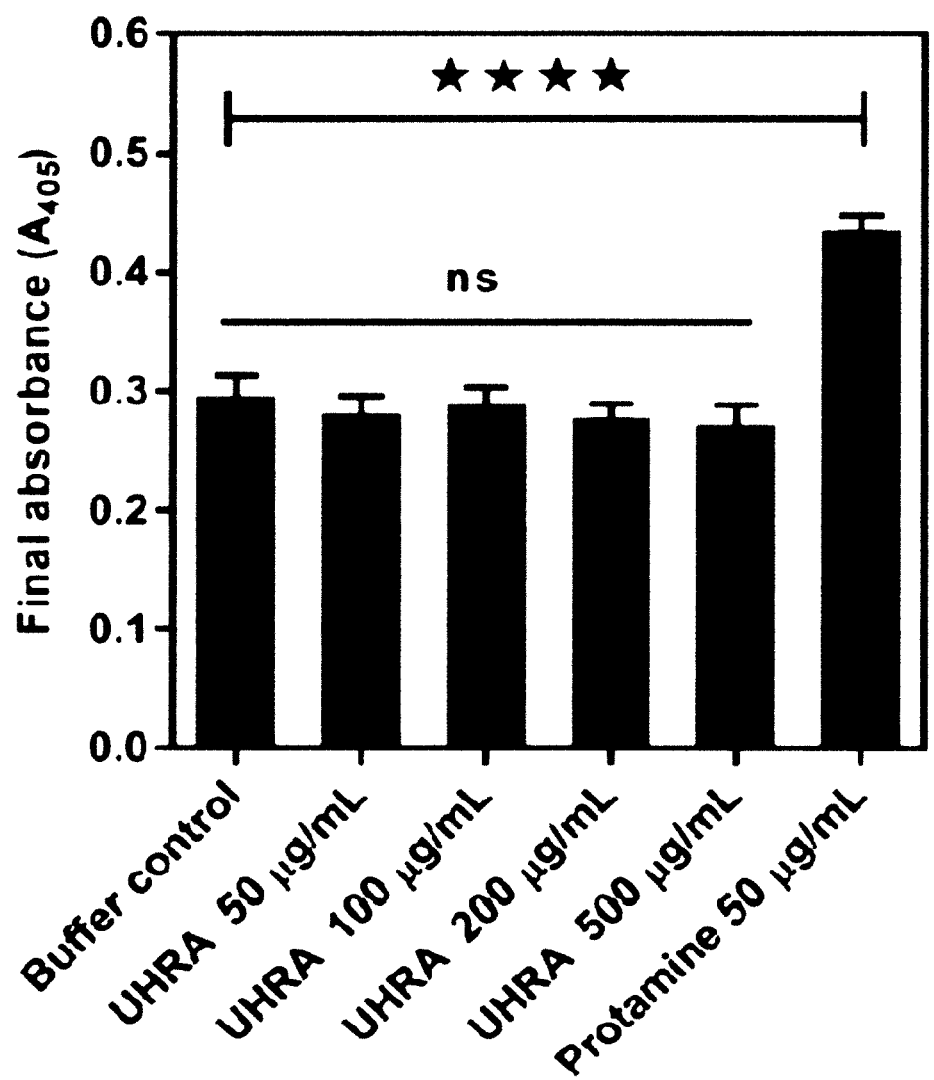
FIG. 11 shows the final turbidity of matured fibrin clots produced from purified fibrinogen in presence of UHRA 8 or PS, where even at 500 μg/mL, UHRA 8 did not increase the final turbidity in comparison to PS at 50 μg/mL suggesting that fibrin polymerization is not affected in presence of UHRA 8,****P<0.0005.
Figure 12:
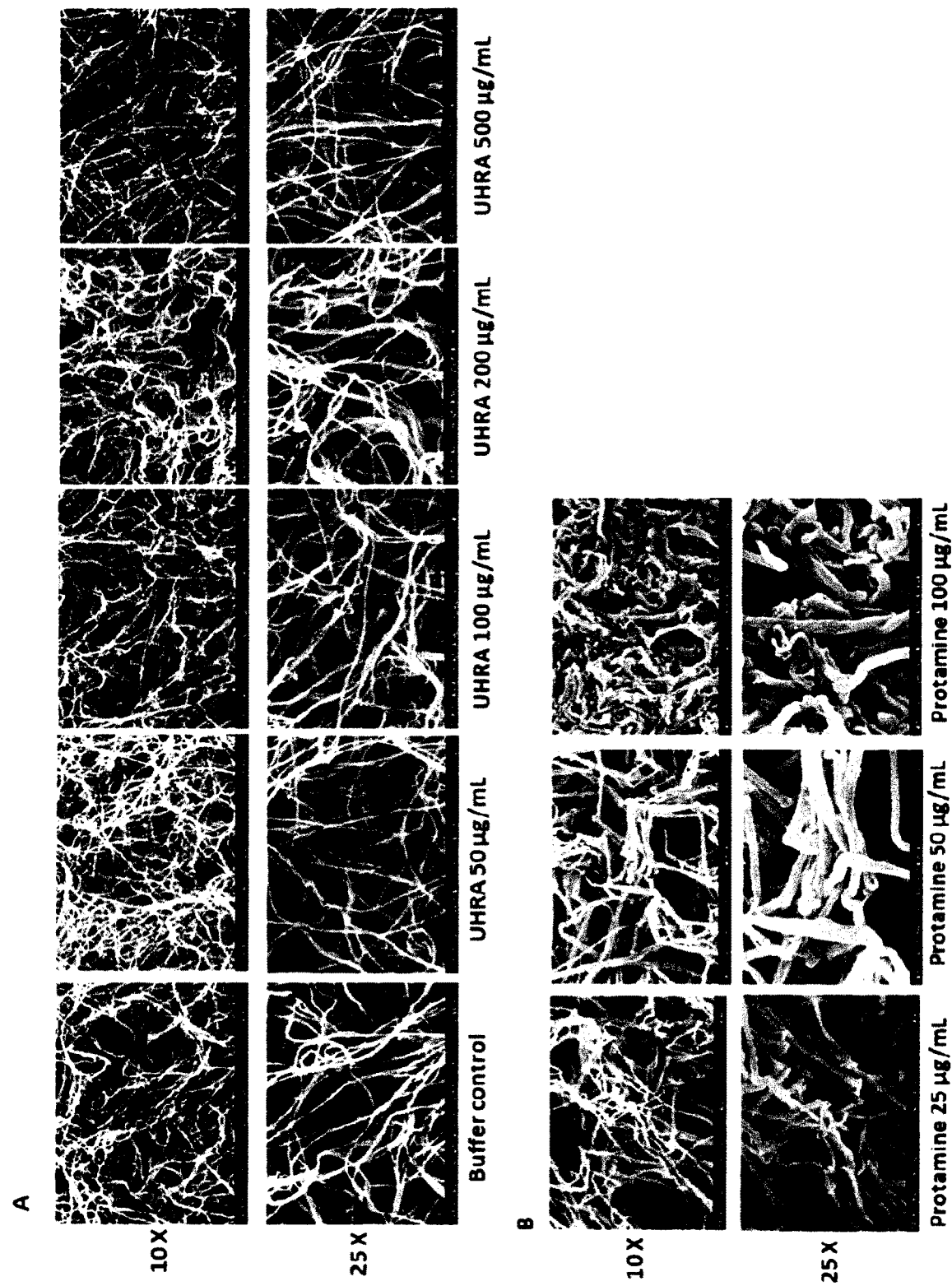
FIG. 12 shows that UHRA 8 does not alter fibrin clot morphology and fiber size, where clots were made by incubating 3 mg/mL of human fibrinogen in the presence of 3.0 mM $CaCl_2$ plus UHRA 8 or PS and the clotting was initiated with 2.5 NIHU/mL of thrombin, clots were then allowed to mature for 1 hour and then processed for scanning electron microscopy (SEM) imaging: (A) shows scanning electron micrographs of fibrin clots formed in presence of UHRA 8 at different concentrations (50 to 500 μg/mL), where even in presence of 500 μg/mL of UHRA 8 gave similar clot architecture as that of the control fibrin clot with both low (10,000× (shown as 10×)) and high (25,000× (shown as 25×)) magnifications; (B) shows scanning electron micrographs of fibrin clots formed in presence of PS at different concentrations (25 to 100 μg/mL), where the fibrin clot formed in presence of PS even at 25 μg/mL has structural variations compared to the control clot; and (C) shows that fibrin fiber thickness of the clot formed in presence of UHRA 8 or PS, where the fiber thickness is measured from scanning electron micrographs using ImageJ software. Fibrin fibers formed in the presence of 25 μg/mL of PS are significantly thicker than the control. ***p<0.0001.
Figure 12:
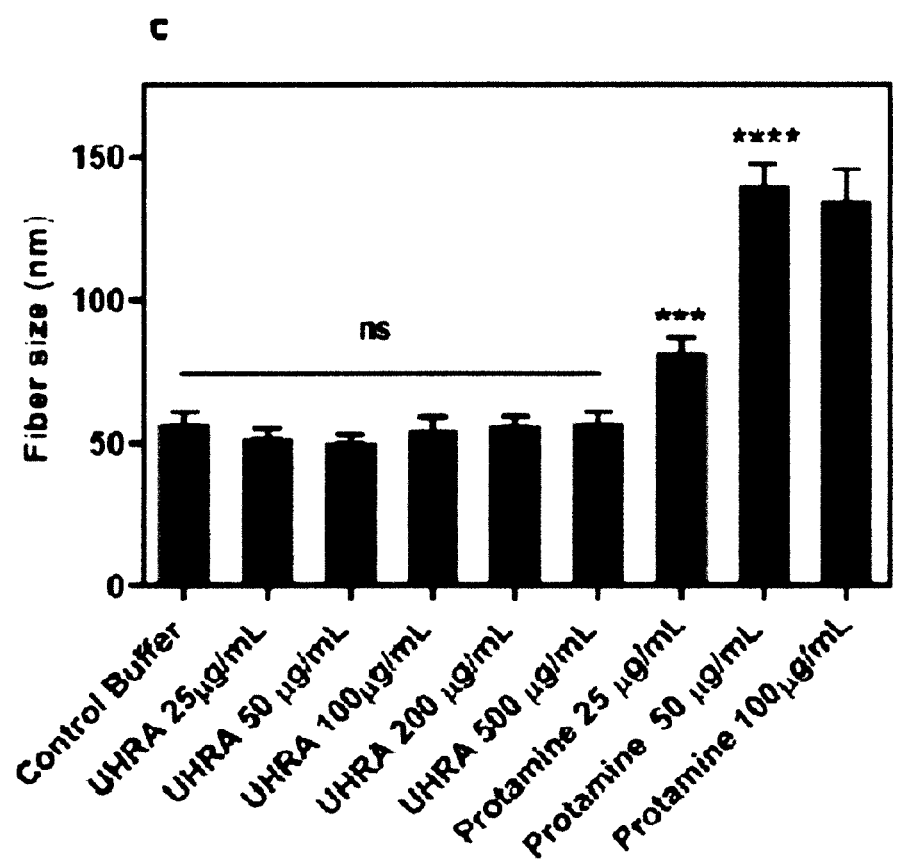

Example 6: UHRA 8 has Negligible Impact on Fibrin Clot and Whole Blood Clot Structure UHRA 8 and protamine sulfate (PS) were tested on fibrin clot architecture by analyzing the clots obtained in the presence of UHRA or PS using scanning electron microscopy in purified system. It was anticipated that polycationic molecules could alter the clot structure due to the non-specific binding (35). As shown in FIG. 12, fibrin clots formed in the presence of UHRA did not induce any significant alteration to the fibrin clot architecture and was homogeneous in comparison to the control even at a concentration as high as 500 μg/mL. In addition, no effect of UHRA 8 was observed on the mean fiber diameter (P=0.12) (FIG. 12C) and was similar to the control buffer added system. This was consistent with our hypothesis that UHRA 8 has minimal non-specific interaction with proteins. On the other hand, PS even at 25 μg/mL increased the mean fiber diameter dramatically (P<0.0001), which again corroborate with the non-specific interaction of PS with the clotting system. The fiber diameter increased with increase in PS concentration. The fibrin clot with thicker fibers formed in the presence of PS correlate to the elevated final turbidity ($A_{405}$) of clots recorded in the fibrin polymerization assay (FIG. 11). The clot structure analysis of in presence of UHRA 8 also correlate with fibrin polymerization assay (FIG. 11); it is anticipated that fibrin clot morphology would remain same as the control sample.

To understand the effect of UHRA 8 on whole blood clot morphology, whole blood clots were prepared in the presence of various amounts of UHRA 8 and observed by SEM. Inspection of blood clot image produced with incremental amounts of UHRA showed normal shaped erythrocytes entrapped in fibrin mesh, and abundant fibrin strands anchored to platelet aggregates similar to the control clots. Blood clots formed in the presence of 25 and 50 μg/mL of PS, also showed normal clot signatures. However, in our experimental conditions, impaired clotting/abnormal blood clot morphology was observed at higher PS concentrations (>50 μg/mL).

Figure 13:
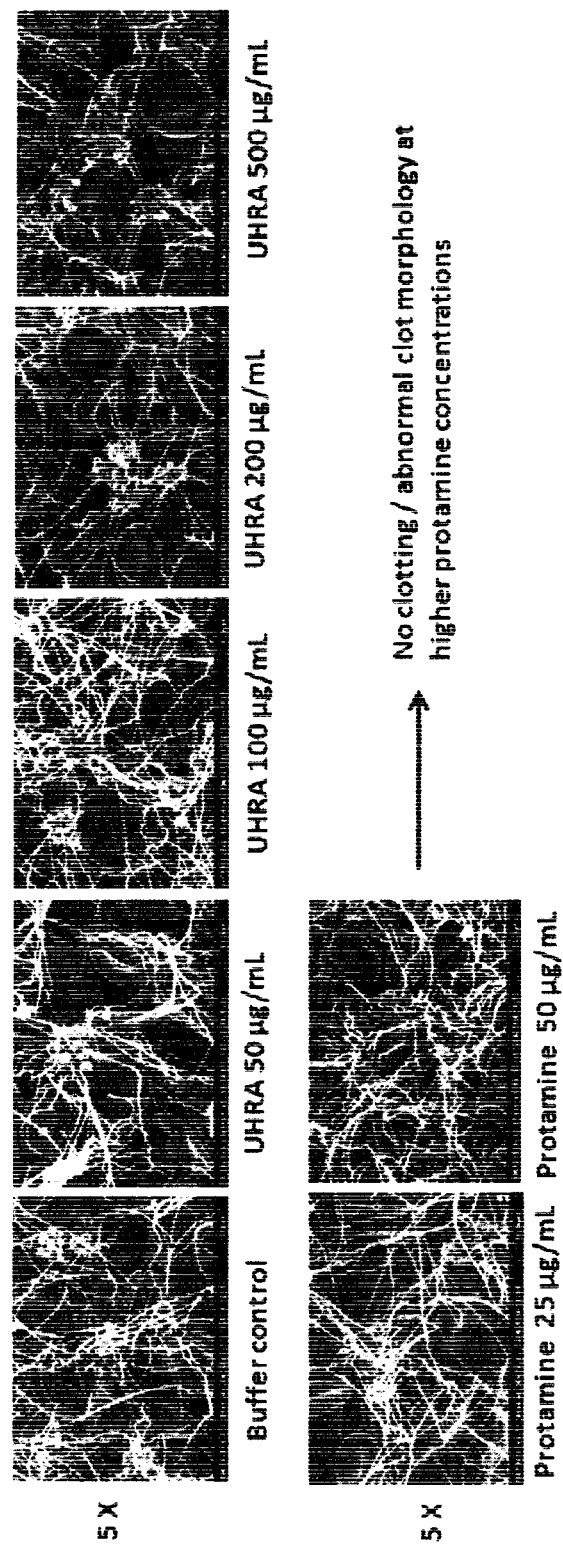
FIG. 13 shows a that blood clot characteristics remain unchanged in the presence of UHRA 8, where clotting was initiated by recalcifying human whole blood with 11.1 mM $CaCl_2$, clot samples were then processed for scanning electron microscopy imaging, where the clots formed in presence of UHRA 8 at 500 μg/mL did not show any major morphological changes. However, abnormal clotting and clot morphology was observed greater than 50 μg/mL of PS (images not shown) (Images were taken at two magnifications 2.5× and 5×, respectively. However, images from only 5× magnification (5,000×) are shown. Respective scale bar is mentioned below the image.)

The activity and amount of thrombin generated are the key elements which influence the formation and morphology of the blood clot (36). Previous studies have shown that thrombin generation in human plasma and its activity is influenced by polycationic macromolecules such as PS (37, 38). To test whether UHRA has any influence on the activity of thrombin, we assessed the activity of thrombin by measuring the ability of thrombin (0.5 NIHU/mL) to cleave a chromogenic peptide substrate following incubation with UHRA. When tested at 100 μg/mL and 200 μg/mL concentration of UHRA 8, we did not observe a change in the initial rate of chromophore release from the substrate by thrombin demonstrating the fact that UHRA 8 does not affect the activity of thrombin (data not shown). This data is corroborated with the normal whole blood clot structure reported in the case of UHRA 8 (FIG. 13).

Previous reports confirm that impaired thrombin generation is one of the factors responsible for the intrinsic anticoagulant property of PS. So, we evaluated the impact of UHRA 8 on TF-initiated thrombin generation by performing a fluorogenic thrombin generation assay in pooled human PRP. Upon clotting of normal human PRP titrated with 100 and 200 μg/mL concentration of UHRA 8, we did not observe any significant changes in parameters such as endogenous thrombin potential (ETP) and amount of thrombin generated (data not shown). This shows that at both tested concentrations, UHRA 8 has no impact on thrombin generation unlike conventional polycations, and is contributing to the formation of normal whole blood clot structure in presence of UHRA 8.

Figure 14:
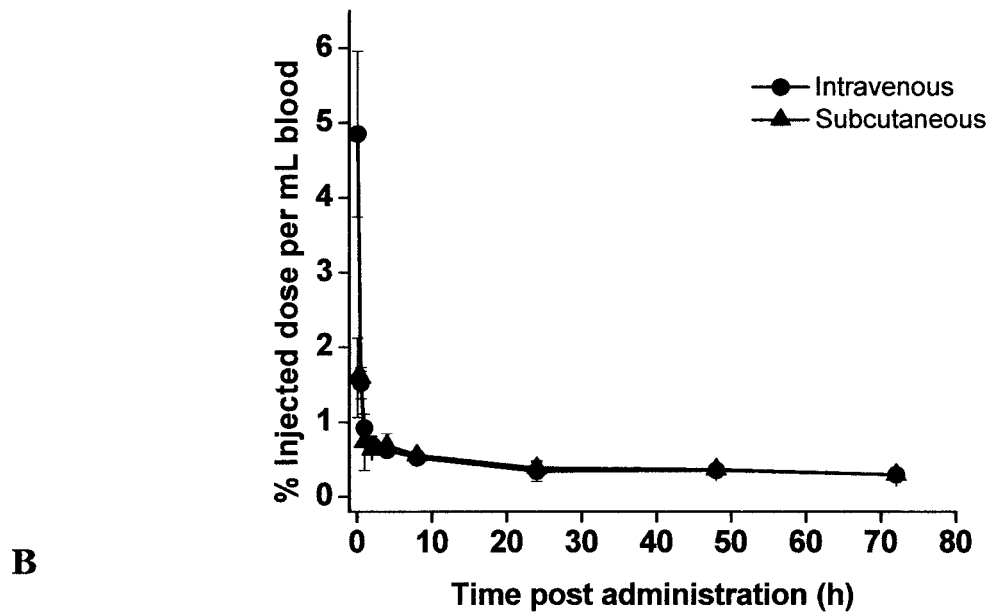
FIG. 14 shows biodistribution in female Balb/C mice after intravenous and subcutaneous administration of 20 mg/kg of tritiated UHRA-10, based on radioactivity in blood (A) and plasma (B). Due to the low molecular weight and smaller size of UHRA-10, the polymer is rapidly cleared from the circulation.
Figure 14:
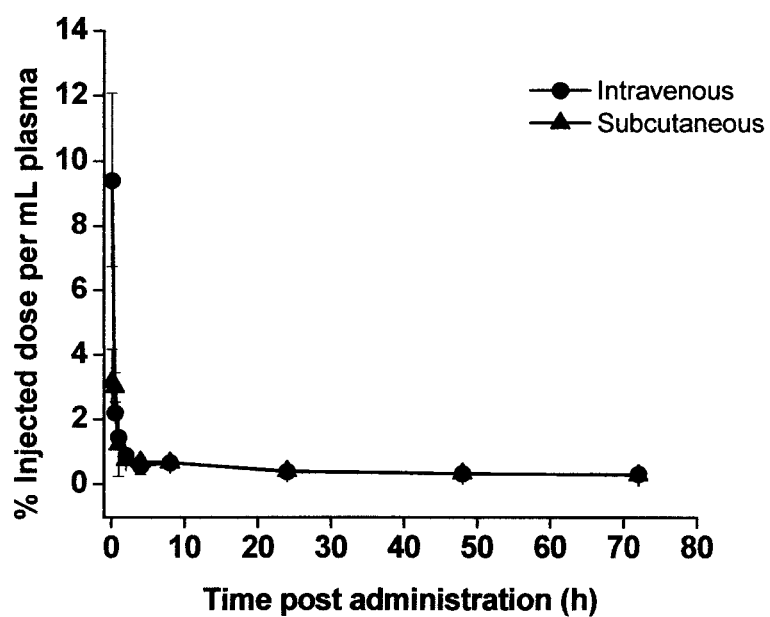
Figure 15:
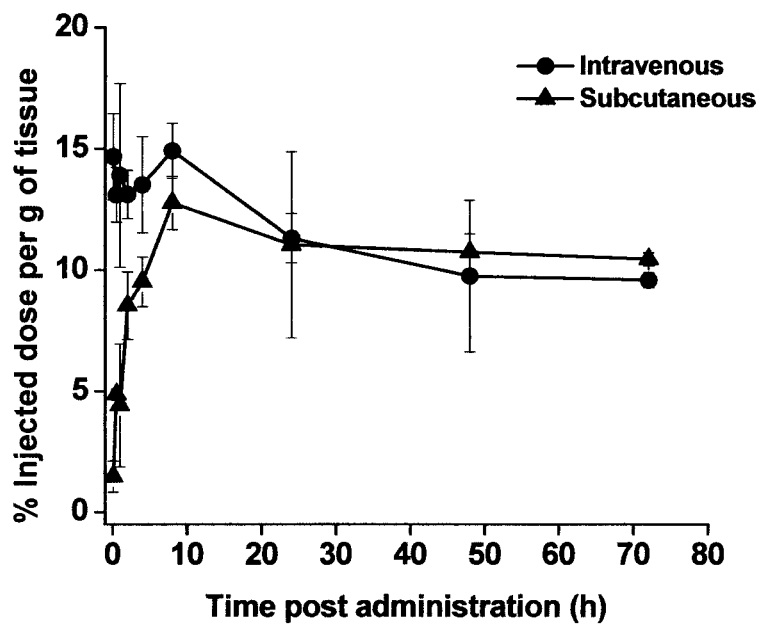
FIG. 15 shows the biodistribution in female Balb/C mice after intravenous and subcutaneous administration of 20 mg/kg of tritiated UHRA-10. The radioactivity in the liver (A), spleen (B), kidneys (C), lungs (D) and heart (E), which shows very low accumulation of UHRA-10 (10% of the injected dose) in liver, (5-7% of the injected dose) in spleen and <5% in kidneys, lungs and heart.
Figure 15:
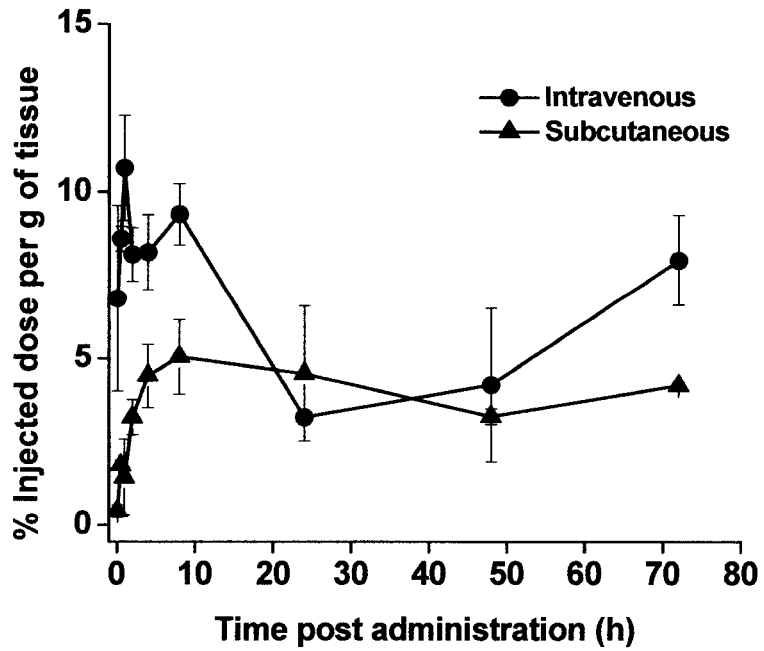
Figure 15:
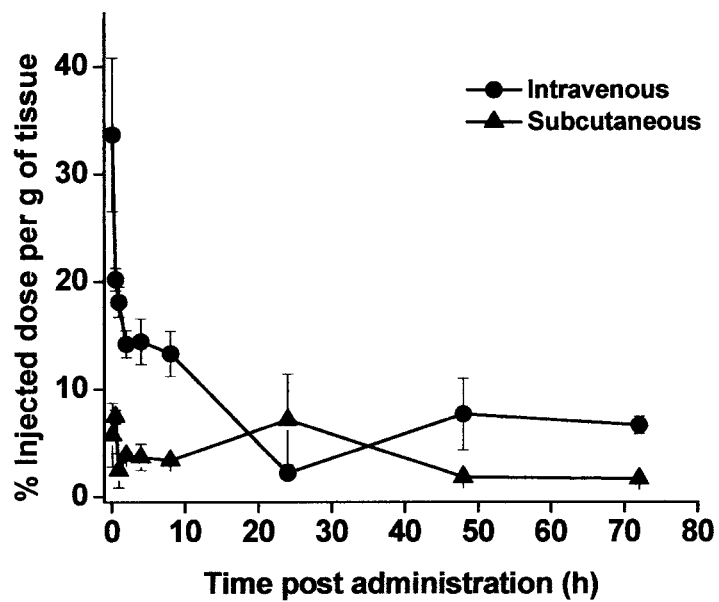
Figure 15:
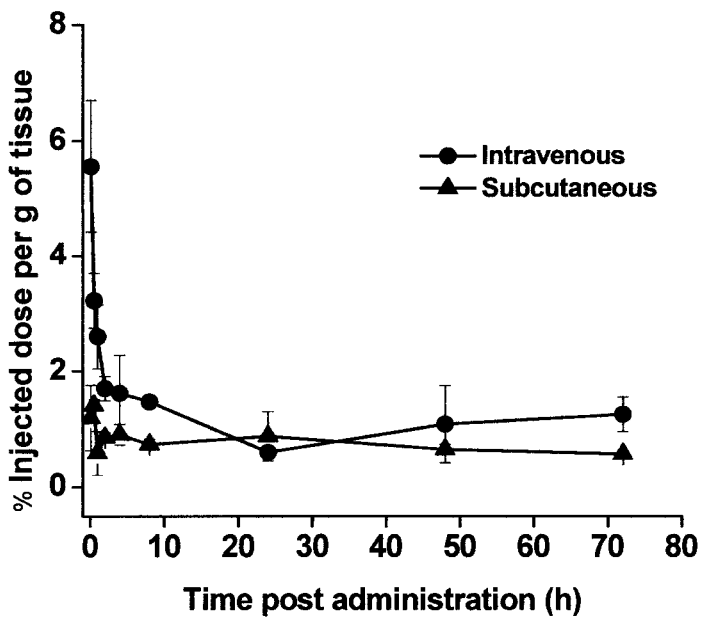
Figure 15:
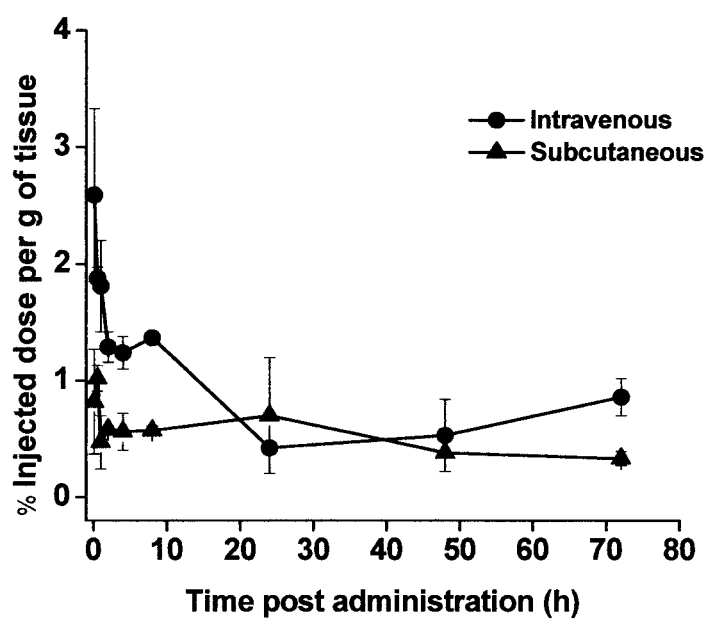

Example 7: Biodistribution and Clearance Data for UHRA-10 by Intravenous and Subcutaneous Administration Biodistribution studies with tritiated UHRA were conducted in female Balb/C mice by administration via the intravenous and subcutaneous routes. As shown in FIG. 14 UHRA 10 when administered at a dose of 20 mg/kg was cleared from circulation over a period of time following intravenous or subcutaneous injections into test mice. Similarly, as shown in FIG. 15 there was minimal UHRA 10 accumulated in liver (A), spleen (B), kidneys (C), lungs (D) and heart (E) following intravenous or subcutaneous injections into test mice. Specifically, there was very low accumulation of UHRA-10 in liver (10% of the injected dose), in spleen (5-7% of the injected dose) and in kidneys, lungs and heart (<5%).

Similarly, as shown in TABLES 4 and 5 the clearance of 20 mg/kg of tritiated UHRA-10 from female Balb/C mice after intravenous and subcutaneous administration is shown as the percentage of injected dose excreted via the urine and feces. Following intravenous administration, 50% injected dose of UHRA-10 is cleared from animal over 72 h. About 32% injected dose of UHRA-10 is cleared from mice following subcutaneous administration.

TABLE 4

Clearance of UHRA 10 via Excretion into the Urine

| Time | % Injected dose in urine | |
|---|---|---|
| (h) | Intravenous | Subcutaneous |
| 2 | 2.90 | 2.29 |
| 4 | 4.02 | 5.47 |
| 8 | 7.16 | 2.32 |
| 24 | 15.93 | 13.02 |
| 48 | 2.87 | 2.89 |
| 72 | 0.77 | 0.69 |
| Total | 33.65 | 26.69 |

TABLE 5

Clearance of UHRA 10 via Excretion into the Feces

| Time | % Injected dose in feces | |
|---|---|---|
| (h) | Intravenous | Subcutaneous |
| 0.5 | 0.015 | 0.008 |
| 1 | 0.499 | 0.023 |
| 2 | 2.523 | 0.199 |
| 4 | 3.586 | 1.101 |
| 8 | 1.840 | 0.830 |
| 24 | 1.963 | 0.642 |
| 48 | 6.607 | 0.365 |
| 72 | 0.015 | 1.586 |
| Total | 17.03 | 4.75 |

Biodistribution studies using tritium labelled UHRA (23 kDa) gave plasma circulation of about 40 minutes with very low accumulation in vital organs (about 8% of the ID in the liver and 2% in spleen, kidney, heart and lung after 48 h) and was cleared mainly via kidney. All these data demonstrated the safety of the UHRAs in vivo when compared to the conventional cationic polymers.

Example 8: Reversal of Procoagulant Activities of Extracellular Nucleic Acids Acid Using UHRA-8

Figure 16A:
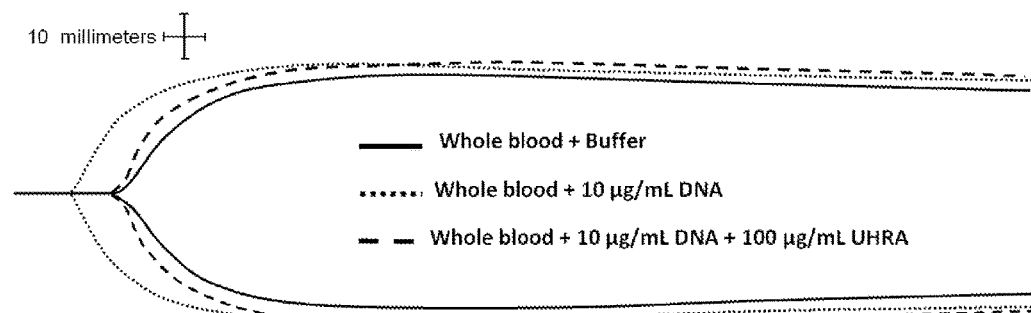
FIG. 16A shows a thromboelastograph trace obtained after performing whole blood TEG analysis with nucleic acid and UHRA-8.
Figure 16B:
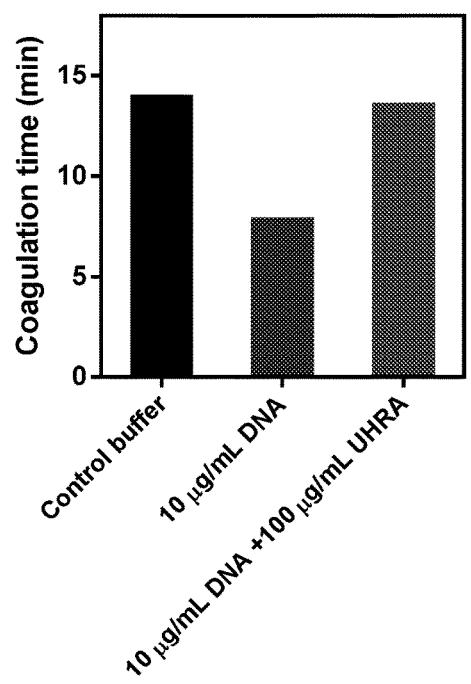
FIG. 16B shows the coagulation time parameter obtained from TEG analysis, where the incubation of nucleic acid with whole blood reduced the clotting time demonstrating the prothrombotic potential of isolated nucleic acid, but clotting time was normalized in the presence of UHRA-8 demonstrating the inhibition of prothrombotic activity of nucleic acid by UHRA molecule.

Blood spiked with 10 μg/mL of nucleic acid showed prothrombotic action. Clotting time was reduced in comparison to the control, but when UHRA-8 was added to the blood containing nucleic acid, the clotting time was comparable to that of buffer control (FIG. 16B). This shows that UHRA has the potential to neutralize the prothrombotic action of nucleic acid. Similarly, the TEG trace also shows that clots formed in the presence of UHRA-nucleic acid complexes are stable and has no profibrinolytic effect (FIG. 16A).

PolyP inhibitors have recently emerged as intriguing candidates for antithrombotic therapies with a novel mode of action that differs dramatically from that of conventional antithrombotic drugs (8, 9). We now report the successful application of a new molecular scaffold (UHRA) for developing antithrombotic agents that target polyP. UHRAs are dendrimer-like compounds engineered to contain multiple positively charged, branched tertiary amines shielded by a protective layer of short-chain PEG groups. Binding of polycationic UHRA compounds to highly anionic polyP is likely dominated by electrostatic interactions. Indeed, when a library of 16 UHRA compounds containing from 1 to 33 R groups was examined (with each R group containing four tertiary amines), we found that their ability to inhibit thrombin/polyP binding was influenced by the number of R groups in the compound, with the most potent inhibitors ($IC_{50}$ values in the low nM range) requiring the presence of ≥5 such R groups. Initially the focus of our attention was on four highly potent UHRA compounds (UHRA 8, 9, 10 and 14; ranging from 7 to 24 R groups per molecule) for more detailed studies. These four compounds strongly inhibited clotting of plasma initiated by both long-chain polyP and RNA (another procoagulant polyanion (14)), albeit with 12- to 24-fold higher potency toward polyP than RNA.

When tested in a small-vessel arterial thrombosis model (laser-induced injury of cremaster arterioles), all four UHRA compounds resulted in lower median levels of accumulation of platelets and fibrin in thrombi compared to saline-treated controls, although the reductions were statistically significant only for UHRA 9 and 10. UHRA 14 has the same MW as UHRA 10 but has a lower charge density (with 7 R groups in the former and 11 in the latter), and indeed, UHRA 14 was a less effective antithrombotic in vivo than was UHRA 10. Interestingly, UHRA 8, which was consistently the best polyP inhibitor in vitro, did not perform as well as UHRA 9 or 10 in vivo. UHRA 8 has the highest molecular weight of the four UHRAs that were tested in vivo, and one can speculate perhaps the smaller UHRAs can better access the interior of forming thrombi.

Higher concentrations of UHRA 10 were needed to inhibit thrombus formation in the $FeCl_3$-induced carotid injury model, a finding consistent with previous studies reporting that complete inhibition of arterial thrombosis caused by injury with 5% $FeCl_3$ necessitates antithrombotic therapy at doses high enough to induce bleeding problems (15). Laser-induced thrombosis in mouse cremaster arterioles on the other hand has been shown to be sensitive to intervention at more clinically relevant levels of antithrombotic therapy (16, 17).

In previous toxicity studies (33), UHRAs did not show hemolysis and red blood cell aggregation even at 5 mg/mL while protamine and PEI induced significant hemolysis. UHRAs compounds also did not show any effect on thrombin generation in human platelet rich plasma. UHRAs are well tolerated in mice after intravenous injection with no adverse effect up to 200 mg/kg (the maximum injected dose) in vivo and the maximum tolerated dose was not reached. In addition, mice injected with 200 mg/kg UHRA had normal serum lactate dehydrogenase (LDH) levels and there were no abnormalities observed in necropsy analysis. Histopathology analysis of the organs 29 days after administration also did not show any tissue damage, necrosis or inflammation, confirming the non-toxic nature of the UHRAs. Protamine, on the other hand, was only tolerated up to 20 mg/kg.

This low toxicity profile for UHRA compounds makes them more attractive for clinical use than polyP inhibitors such as polyethylenimine, protamine, polymyxin B or PAMAM dendrimers (8, 9), many of which contain multiple primary amines. Polymyxin B has well-known toxicity in humans and is currently considered a treatment of last resort in sepsis cases (18). Protamine has demonstrated toxicity as well, including anticoagulant effects in the absence of heparin (19, 20) and ability to precipitate fibrinogen at high concentrations (21). Interestingly, cationic PAMAM dendrimers have also been shown to interact with and precipitate fibrinogen in solution (11), which was confirmed in this study. UHRA compounds showed no signs of these adverse interactions at concentrations of up to 1.5 mg/mL.

The non-toxic and modular nature of UHRA compounds like the ones investigated in this study makes them attractive candidates for the development of clinical antithrombotic agents with a novel mode of action. While we cannot conclusively say that the antithrombotic nature of these compounds is entirely based on their ability to bind to polyP and inhibit its role in thrombus formation in vivo, doses of the compound that are well-tolerated in mice were as effective as heparin in inhibiting thrombosis but with less bleeding side effects than with heparin. While heparin and heparin derivatives are some of the most widely used antithrombotics today, they have well-documented drawbacks that extended even beyond the bleeding risks (5, 22).

Although the compounds that were used in this study were effective both in vitro and in vivo in attenuating thrombus formation, compounds are contemplated that have more or less specificity for polyP versus other anionic polymers like extracellular nucleic acids, which have also been implicated in pathological thrombosis (9, 23). These could be used in a variety of antithrombotic therapeutics that could be used to more efficiently treat the different causes of thrombosis in individual patients. We contemplate using polyP inhibitors in sepsis and disseminated intravascular coagulation, where not only platelet polyP but also long-chain polyP from infectious microorganisms might play roles in pathological thrombus formation. Microbial (long-chain) polyP is orders of magnitude more effective than platelet polyP at triggering the contact pathway of blood clotting and can induce multiple inflammatory reactions (24-28).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings. Unless otherwise explained, all technical and scientific terms used herein have the same meaning as commonly understood by one of ordinary skill in the art to which a disclosed disclosure belongs.

The disclosure may be further understood by the following non-limiting examples. Although the description herein contains many specific examples, these should not be construed as limiting the scope of the disclosure but as merely providing illustrations of some of the embodiments of the disclosure. For example, thus the scope of the disclosure should be determined by the appended aspects and their equivalents, rather than by the examples given.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this disclosure for a given application. In specific applications, the selection of a given anion or cation for preparation of a salt may result in increased or decreased solubility of that salt. Every formulation or combination of components described or exemplified herein may be used to practice the disclosure, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

REFERENCES

1. Rao N N, Gomez-Garcia M R, and Kornberg A. Inorganic Polyphosphate: Essential for Growth and Survival. Annual Review of Biochemistry. 2009; 78(605-47.
2. Ruiz F A, Lea C R, Oldfield E, and Docampo R. Human platelet dense granules contain polyphosphate and are similar to acidocalcisomes of bacteria and unicellular eukaryotes. J Biol Chem. 2004; 279(43):44250-7.
3. Morrissey J H, Choi S H, and Smith S A. Polyphosphate: an ancient molecule that links platelets, coagulation, and inflammation. Blood. 2012; 119(25):5972-9.
4. McFadyen J D, and Jackson S P. Differentiating haemostasis from thrombosis for therapeutic benefit. Thrombosis and haemostasis. 2013; 110(5):859-67.
5. Gurbuz H A, Durukan A B, Sevim H, Ergin E, Gurpinar A, and Yorgancioglu C. Heparin toxicity in cell culture: a critical link in translation of basic science to clinical practice. Blood coagulation & fibrinolysis: an international journal in haemostasis and thrombosis. 2013; 24(7): 742-5.
6. Tessler O, Vorstenbosch J, Jones D, Lalonde S, and Zadeh T. Heparin-induced thrombocytopenia and thrombosis as an under-diagnosed cause of flap failure in heparin-naive patients: A case report and systematic review of the literature. Microsurgery. 2014; 34(2):157-63.
7. Dasararaju R, Singh N, and Mehta A. Heparin induced thrombocytopenia: review. Expert review of hematology. 2013; 6(4):419-28.
8. Smith S A, Choi S H, Collins J N, Travers R J, Cooley B C, and Morrissey J H. Inhibition of polyphosphate as a novel strategy for preventing thrombosis and inflammation. Blood. 2012; 120(26):5103-10.
9. Jain S, Pitoc G A, Holl E K, Zhang Y, Borst L, Leong K W, Lee J, and Sullenger B A. Nucleic acid scavengers inhibit thrombosis without increasing bleeding. Proc Natl Acad Sci USA. 2012; 109(32):12938-43.
10. Jain K, Kesharwani P, Gupta U, and Jain N K. Dendrimer toxicity: Let's meet the challenge. International journal of pharmaceutics. 2010; 394(1-2):122-42.
11. Jones C F, Campbell R A, Brooks A E, Assemi S, Tadjiki S, Thiagarajan G, Mulcock C, Weyrich A S, Brooks B D, Ghandehari H, et al. Cationic PAMAM dendrimers aggressively initiate blood clot formation. ACS nano. 2012; 6(11):9900-10.
12. Chauhan A S, Jain N K, and Diwan P V. Pre-clinical and behavioural toxicity profile of PAMAM dendrimers in mice. Proceedings of the Royal Society A: Mathematical, Physical and Engineering Science. 2010; 466(2117): 1535-50.
13. Sadekar S, and Ghandehari H. Transepithelial transport and toxicity of PAMAM dendrimers: implications for oral drug delivery. Adv Drug Deliv Rev. 2012; 64(6):571-88.
14. Kannemeier C, Shibamiya A, Nakazawa F, Trusheim H, Ruppert C, Markart P, Song Y, Tzima E, Kennerknecht E, Niepmann M, et al. Extracellular RNA constitutes a natural procoagulant cofactor in blood coagulation. Proc Natl Acad Sci USA. 2007; 104(15):6388-93.
15. Wang X, and Xu L. An optimized murine model of ferric chloride-induced arterial thrombosis for thrombosis research. Thrombosis research. 2005; 115(1-2):95-100.
16. Furie B, and Furie B C. In vivo thrombus formation. Journal of thrombosis and haemostasis: JTH. 2007; 5 Suppl 1(12-7.
17. Jasuja R, Passam F H, Kennedy D R, Kim S H, van Hessem L, Lin L, Bowley S R, Joshi S S, Dilks J R, Furie B, et al. Protein disulfide isomerase inhibitors constitute a new class of antithrombotic agents. The Journal of clinical investigation. 2012; 122(6):2104-13.
18. Keirstead N D, Wagoner M P, Bentley P, Blais M, Brown C, Cheatham L, Ciaccio P, Dragan Y, Ferguson D, Fikes J, et al. Early prediction of polymyxin-induced nephrotoxicity with next-generation urinary kidney injury biomarkers. Toxicological sciences: an official journal of the Society of Toxicology. 2014; 137(2):278-91.
19. Nielsen V G. Protamine enhances fibrinolysis by decreasing clot strength: role of tissue factor-initiated thrombin generation. The Annals of thoracic surgery. 2006; 81(5):1720-7.
20. Von Kaulla K N. Intravenous protein-free pyrogen; a powerful fibrinolytic agent in man. Circulation. 1958; 17(2):187-98.
21. Stewart G J, and Niewiarowski S. Nonenzymatic polymerization of fibrinogen by protamine sulfate. An electron microscope study. Biochimica et biophysica acta. 1969; 194(2):462-9.
22. Jennewein C, Paulus P, and Zacharowski K. Linking inflammation and coagulation: novel drug targets to treat organ ischemia. Current opinion in anaesthesiology. 2011; 24(4):375-80.
23. Fuchs T A, Brill A, Duerschmied D, Schatzberg D, Monestier M, Myers D D, Wrobleski S K, Wakefield T W, Hartwig J H, and Wagner D D. Extracellular DNA traps promote thrombosis. Proceedings of the National Academy of Sciences of the United States of America. 2010; 107(36):15880-5.
24. Smith S A, Choi S H, Davis-Harrison R, Huyck J, Boettcher J, Reinstra C M, and Morrissey J H. Polyphosphate exerts differential effects on blood clotting, depending on polymer size. Blood. 2010; 116(20):4353-9.
25. Semeraro F, Ammollo C T, Morrissey J H, Dale G L, Friese P, Esmon N L, and Esmon C T. Extracellular histones promote thrombin generation through platelet-dependent mechanisms: involvement of platelet TLR2 and TLR4. Blood. 2011; 118(7):1952-61.
26. Smith S A, and Morrissey J H. Polyphosphate enhances fibrin clot structure. Blood. 2008; 112(7):2810-6.
27. Yun T H, and Morrissey J H. Polyphosphate and omptins: novel bacterial procoagulant agents. Journal of Cellular and Molecular Medicine. 2009; 13(10):4146-53.
28. Muller F, Mutch N J, Schenk W A, Smith S A, Esterl L, Spronk H M, Schmidbauer S, Gahl W A, Morrissey J H, and Renne T. Platelet polyphosphates are proinflammatory and procoagulant mediators in vivo. Cell. 2009; 139(6):1143-56.
29. Choi S H, Collins J N, Smith S A, Davis-Harrison R L, Rienstra C M, and Morrissey J H. Phosphoramidate end labeling of inorganic polyphosphates: facile manipulation of polyphosphate for investigating and modulating its biological activities. Biochemistry. 2010; 49(45):9935-41.
30. Jones C F, Campbell R A, Brooks A E, Assemi S, Tadjiki S, Thiagarajan G, Mulcock C, Weyrich A S, Brooks B D, Ghandehari H, et al. Cationic PAMAM dendrimers aggressively initiate blood clot formation. ACS nano. 2012; 6(11):9900-10.
31. Burgess E A, Sylven B. Glucose, lactate, and lactic dehydrogenase activity in normal interstitial fluid and that of solid mouse tumors. Cancer Res. 1962; 22:581-588.
32. Hayashi T, Salata K, Kingman A, Notkins A L. Regulation of enzyme levels in the blood. Influence of environmental and genetic factors on enzyme clearance. Am J Pathol. 1988; 132(3):503-511.
33. Shenoi R A, Kalathottukaren M T, Travers R J, Lai B F L, Creagh A L, Lange D, Yu K, Weinhart M, Chew B, Du C, Brooks D E, Carter C J, Morrissey J H, Haynes C A, and Kizhakkedathu J N. Affinity-based design and discovery of a synthetic universal reversal agent for clinically used parenteral heparin anticoagulants Sci Transl Med (2014) 6(260): 260ra150.
34. WO2012/162789 Polymers for Reversing Heparin-based Anticoagulation.
35. Zhong D, Jiao Y, Zhang Y, et al. Effects of the gene carrier polyethyleneimines on structure and function of blood components. Biomaterials. 2013; 34:294-305.
36. Wolberg A S. Thrombin generation and fibrin clot structure. Blood reviews. 2007; 21:131-142.

37. Ainle F N, Preston R J S, Jenkins V P, et al. Protamine sulphate down-regulates thrombin generation by inhibiting factor V activation. Blood. 2009; 114: 1658-1665.

38. Cobel-Geard and Hassouna H I. Interaction of protamine sulfate with thrombin. American Journal of Hematology. 1983; 14:227-233.

39. Travers R J, Shenoi R A, Kalathottukaren M T, Kizhakkedathu J N, Morrissey J H. Nontoxic polyphosphate inhibitors reduce thrombosis while sparing hemostasis. Blood. 2014 Nov. 20; 124(22):3183-90. doi: 10.1182/blood-2014-05-577932. Epub 2014 Sep. 8.

What is claimed is:

1. A method of binding a phosphate containing biological macromolecule, the method comprising administering a Universal Heparin Reversal Agent (UHRA) polymer to a subject in need of having phosphate containing biological macromolecules bound, wherein the UHRA polymer comprises: a) a dendritic polyglycerol core having 5-33 randomly distributed tetra-amine groups, wherein the tetra-amines have the following structure

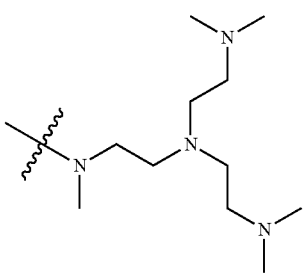 [SMILES: *N(C)CCN(CCN(C)C)CCN(C)C]

and wherein the molecular weight of the polymer in kDa per tetra-amine group does not exceed 4.5; and (b) an outer shell, wherein the outer shell is a hydrophilic polymeric system, wherein the hydrophilic polymeric system is selected from the group consisting of polyether, polyalcohol, polyglycerol, linear polyglycerol, oligosaccharide, poly(N-isopropylacrylamide (PNIPAM), polyacrylamide (PAM), poly(2-oxazoline), poly(ethylene glycol), methoxy(polyethylene glycol), poly(ethylene oxide), poly(vinyl alcohol) (PVA), and poly(vinylpyrrolidone) (PVP), and combinations thereof, and wherein the UHRA polymer is selected from the group consisting of UHRA-1, UHRA-2, UHRA-5, UHRA-6, UHRA-7, UHRA-8, UHRA-9, UHRA-10, UHRA-11, UHRA-13, UHRA-14 and UHRA-15.

2. The method of claim 1, wherein the outer shell is selected from one or more of:

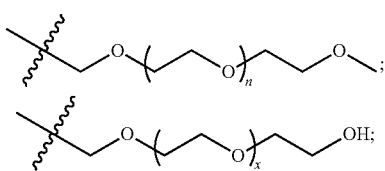

or

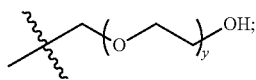

wherein
n is 0-100, x is 0-100 and y is 0-100;
n is an integer between 1 and 20, x is an integer between 1 and 20 and y is an integer between 1 and 20;
n is an integer between 3 and 10, x is an integer between 3 and 10 and y is an integer between 3 and 10;
n is an integer between 4 and 9, x is an integer between 4 and 9 and y is an integer between 4 and 9;
or
n is an integer between 5 and 8, x is an integer between 5 and 8 and y is an integer between 5 and 8.

3. The method of claim 1, wherein the binding of the phosphate containing biological macromolecule results in neutralization.

4. The method of claim 1, wherein the phosphate containing biological macromolecule is polyphosphate or a nucleic acid.

5. The method of claim 4, wherein the binding to polyphosphate disrupts the interaction between thrombin and polyphosphate.

6. The method of claim 1, wherein the polyglycerol core has between 7-24 randomly distributed tetra-amine groups or wherein the polyglycerol core has between 11-24 randomly distributed tetra-amine groups.

7. The method of claim 1, wherein the molecular weight of the UHRA polymer in kDa per tetra-amine group is between 0.9 and 4.5 or wherein the molecular weight of the UHRA polymer in kDa per tetra-amine group does not exceed 3.6.

8. The method of claim 1, wherein the UHRA polymer has an $IC_{50}$ (nM) for inhibition of thrombin binding to polyphosphate is equal to or less than 50 nM.

9. The method of claim 1, wherein the polyglycerol core has a degree of branching: in the range of about 0.05 to about 0.95; or in the range of about 0.40 to about 0.65.

10. The method of claim 1, wherein the subject is administered the UHRA polymer to treat stroke, acute coronary syndrome, pulmonary embolism, atrial fibrillation, venous or arterial thromboembolism, disseminated intravascular coagulation (DIC), deep-vein thrombosis (DVT), peripheral artery disease, trauma-induced coagulopathy, extracorporeal circulation, cancer-associated thrombosis, sepsis, septic shock, Systemic Inflammatory Response Syndrome (SIRS), and inflammation.

11. The method of claim 10, wherein the UHRA polymer is administered in a dose range of 1 mg/kg to 1000 mg/kg.

12. The method of claim 10, wherein the UHRA polymer is administered in a dose range of 50-100 mg/kg.

13. The method of claim 10, wherein the subject is human.

14. The method of claim 10, wherein the subject is non-human.

15. The method of claim 14, wherein the subject is a non-human mammal.

16. The method of claim 14, wherein the subject is a mouse, a rat, a pig, a dog, a cat, a horse, a sheep, a cattle, a goat or a chicken.

17. The method of claim 1, wherein shell polymer is between about 10 to about 90 wt % of the UHRA polymer.

* * * * *

UNITED STATES PATENT AND TRADEMARK OFFICE
CERTIFICATE OF CORRECTION

PATENT NO. : 10,202,507 B2
APPLICATION NO. : 15/313774
DATED : February 12, 2019
INVENTOR(S) : Jayachandran Kizhakkedathu Page 1 of 1

It is certified that error appears in the above-identified patent and that said Letters Patent is hereby corrected as shown below:

In the Specification

At Column 17, Line 50, the recitation of "3-phenyipropionic acid" should read "3-phenylpropionic acid".

Signed and Sealed this
Sixteenth Day of April, 2019

Andrei Iancu
*Director of the United States Patent and Trademark Office*